United States Patent
Fiedler et al.

(10) Patent No.: US 10,584,152 B2
(45) Date of Patent: Mar. 10, 2020

(54) BINDING PROTEINS BASED ON DI-UBIQUITIN MUTEINS AND METHODS FOR GENERATION

(71) Applicant: Navigo Proteins GmbH, Halle/Saale (DE)

(72) Inventors: Erik Fiedler, Halle/Saale (DE); Maren Meysing, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 0 days.

(21) Appl. No.: 15/744,054

(22) PCT Filed: Jul. 19, 2016

(86) PCT No.: PCT/EP2016/067216
§ 371 (c)(1),
(2) Date: Jan. 11, 2018

(87) PCT Pub. No.: WO2017/013136
PCT Pub. Date: Jan. 26, 2017

(65) Prior Publication Data
US 2018/0194819 A1    Jul. 12, 2018

(30) Foreign Application Priority Data
Jul. 20, 2015  (EP) .................................. 15177545

(51) Int. Cl.
| | |
|---|---|
| C07K 14/245 | (2006.01) |
| A61K 38/16 | (2006.01) |
| C07K 14/47 | (2006.01) |
| A61K 47/62 | (2017.01) |
| A61K 47/64 | (2017.01) |
| C12N 15/10 | (2006.01) |
| G01N 33/574 | (2006.01) |
| A61K 38/00 | (2006.01) |

(52) U.S. Cl.
CPC ........ *C07K 14/4702* (2013.01); *A61K 38/164* (2013.01); *A61K 47/62* (2017.08); *A61K 47/642* (2017.08); *A61K 47/643* (2017.08); *C07K 14/245* (2013.01); *C07K 14/47* (2013.01); *C12N 15/1093* (2013.01); *G01N 33/57492* (2013.01); *A61K 38/00* (2013.01); *G01N 2333/70596* (2013.01); *G01N 2333/71* (2013.01)

(58) Field of Classification Search
None
See application file for complete search history.

(56) References Cited

U.S. PATENT DOCUMENTS

| | | | |
|---|---|---|---|
| 4,873,192 A | 10/1989 | Kunkel | |
| 5,789,166 A | 8/1998 | Bauer et al. | |
| 5,958,684 A | 9/1999 | Van Leeuwen et al. | |
| 6,217,863 B1 | 4/2001 | Godavarti et al. | |
| 6,569,677 B1 | 5/2003 | Legrand et al. | |
| 6,620,587 B1 | 9/2003 | Taussig et al. | |
| 6,673,901 B2 | 1/2004 | Koide | |
| 6,799,121 B2 | 9/2004 | Chu et al. | |
| 7,250,297 B1 | 7/2007 | Beste et al. | |
| 7,273,924 B1 | 9/2007 | Neil et al. | |
| 7,393,918 B2 | 7/2008 | Golemi-Kota et al. | |
| 7,601,803 B1 | 10/2009 | Fiedler et al. | |
| 7,838,629 B2 | 11/2010 | Fiedler et al. | |
| 7,851,599 B2 | 12/2010 | Menrad et al. | |
| 8,097,254 B2 | 1/2012 | Ned et al. | |
| 8,404,814 B2 | 3/2013 | Neri et al. | |
| 8,426,357 B2 | 4/2013 | Kraehmer et al. | |
| 8,455,625 B2 | 6/2013 | Neri et al. | |
| 8,592,144 B2 | 11/2013 | Fiedler et al. | |
| 8,592,179 B2 | 11/2013 | Schraeml et al. | |
| 8,623,373 B2 | 1/2014 | Zardi et al. | |
| 8,748,351 B2 | 6/2014 | Kunert et al. | |
| 8,790,895 B2 | 7/2014 | Fiedler et al. | |
| 8,791,238 B2 | 7/2014 | Fiedler et al. | |
| 8,921,304 B2 | 12/2014 | Steuernagel et al. | |
| 9,492,572 B2 | 11/2016 | Nerkamp et al. | |
| 2003/0045681 A1 | 3/2003 | Neri et al. | |
| 2003/0073623 A1 | 4/2003 | Drmanac et al. | |
| 2004/0043386 A1 | 3/2004 | Pray et al. | |
| 2006/0058510 A1 | 3/2006 | Skerra et al. | |

(Continued)

FOREIGN PATENT DOCUMENTS

| | | |
|---|---|---|
| AU | 2013318928 | 4/2015 |
| EP | 1 591 527 A1 | 11/2005 |

(Continued)

OTHER PUBLICATIONS

Abedi et al. (1998) Green fluorescent protein as a scaffold for intracellular presentation of peptides. Nucleic Acids Research 26(2):623-630.

(Continued)

*Primary Examiner* — Lianko G Garyu

(74) *Attorney, Agent, or Firm* — Jenkins, Wilson, Taylor & Hunt, P.A.

(57) ABSTRACT

The present invention refers to new binding proteins based on di-ubiquitin modified in 12, 13, or 14 positions selected from positions R42, I44, H68, V70, R72, L73, R74, K82, L84, Q138, K139, E140, S141, and T142 of di-ubiquitin and being able to bind specifically with high affinity to selected targets. Furthermore, the invention provides a method for the generation of said binding proteins. In addition, libraries encoding for said binding proteins based on di-ubiquitin muteins modified in 12, 13, or 14 positions selected from R42, I44, H68, V70, R72, L73, R74, K82, L84, Q138, K139, E140, S141, and T142 are provided.

24 Claims, 11 Drawing Sheets

Specification includes a Sequence Listing.

(56) References Cited

U.S. PATENT DOCUMENTS

| | | |
|---|---|---|
| 2006/0099686 A1 | 5/2006 | Fiedler et al. |
| 2007/0015248 A1 | 1/2007 | Anton et al. |
| 2007/0111287 A1 | 5/2007 | Fiedler et al. |
| 2007/0189963 A1 | 8/2007 | Neri et al. |
| 2007/0248536 A1 | 10/2007 | Fiedler et al. |
| 2007/0286843 A1 | 12/2007 | Pfizenmaier et al. |
| 2008/0171851 A1 | 7/2008 | Fiedler et al. |
| 2010/0119446 A1 | 5/2010 | Grabulovski et al. |
| 2010/0130720 A1 | 5/2010 | Schraeml et al. |
| 2011/0162095 A1 | 6/2011 | Hill et al. |
| 2012/0244596 A1 | 9/2012 | Skerra et al. |
| 2012/0301393 A1 | 11/2012 | Steuernagel et al. |
| 2013/0011334 A1 | 1/2013 | Steuernagel et al. |
| 2013/0097737 A1 | 4/2013 | Kovalic et al. |
| 2013/0157878 A1 | 6/2013 | Kunert et al. |
| 2014/0219959 A1 | 8/2014 | Nerkamp et al. |
| 2015/0183846 A1 | 7/2015 | Lange et al. |
| 2018/0030098 A1 | 2/2018 | Bosse-Doenecke et al. |
| 2018/0030140 A1 | 2/2018 | Bosse-Doenecke et al. |
| 2018/0273636 A1 | 9/2018 | Settele et al. |
| 2018/0305463 A1 | 10/2018 | Haupts |
| 2019/0117791 A1 | 4/2019 | Haupts et al. |
| 2019/0177376 A1 | 6/2019 | Knick et al. |
| 2019/0292266 A1 | 9/2019 | Bosse-Doenecke et al. |

FOREIGN PATENT DOCUMENTS

| | | |
|---|---|---|
| EP | 2 532 672 A2 | 12/2012 |
| EP | 2 727 942 A1 | 5/2014 |
| EP | 2 738 180 | 6/2014 |
| EP | 2829552 A1 | 1/2015 |
| RU | 2134696 C1 | 8/1999 |
| WO | WO 2005/044845 A2 | 5/2005 |
| WO | WO 2007/054120 A1 | 5/2007 |
| WO | WO 2012/171541 A1 | 12/2012 |
| WO | WO 2013/186329 A1 | 12/2013 |
| WO | WO 2014/094799 | 6/2014 |
| WO | WO 2016/124670 A1 | 8/2016 |
| WO | WO 2016/124702 A1 | 8/2016 |
| WO | WO 2017/013129 | 1/2017 |
| WO | WO 2017009421 | 1/2017 |

OTHER PUBLICATIONS

Advisory Action corresponding to U.S. Appl. No. 10/030,605 dated Oct. 13, 2006.
Advisory Action corresponding to U.S. Appl. No. 11/732,632 dated Jun. 30, 2010.
Advisory Action corresponding to U.S. Appl. No. 12/072,959 dated May 18, 2010.
Baker et al. (1994) Protein Expression Using Cotranslational Fusion and Cleavage of Ubiquitin. The Journal of Biological Chemistry 269(41):25381-25386.
Beal et al. (1996) Surface hydrophobic residues of multiubiquitin chains essential for proteolytic targeting. PNAS 93:861-866.
Beste et al. (1999) Small antibody-like proteins with prescribed ligand specificities derived from the lipocalin fold. PNAS 96:1898-1903.
Birchler et al. (1999) Selective targeting and photocoagulation of ocular angiogenesis mediated by a phage-derived human antibody fragment. Nature Biotechnology 17:984-988.
Bofill et al. (2005) Engineering Stabilising beta-Sheet Interactions into a Conformationally Flexible Region of the Folding Transition State of Ubiquitin. Journal of Molecular Biology 353(2):373-384.
Bolton et al. (2001) Structure and Properties of a Dimeric N-terminal Fragment of Human Ubiquitin. Journal of Molecular Biology 314(4):773-787.
Borsi et al. (2003) Selective targeted delivery of TNFα to tumor blood vessels. Blood 102(13):4384-4392.
Brinkmann et al. (1993) A recombinant immunotoxin containing a disulfide-stabilized Fv-fragment. PNAS 90:7538-7542.

Brinkmann et al. (1997) Stabilization of a Recombinant Fv Fragment by Base-Loop Interconnection and VH-VL Permutation. Journal of Molecular Biology 268:107-117.
Buchberger et al. (2001) The UBX Domain: A Widespread Ubiquitin-Like Module. Journal of Molecular Biology 307(1):17-24.
Burch & Haas (1994) Site-directed mutagenesis of ubiquitin. Differential roles for arginine in the interaction with ubiquitin-activating enzyme. Biochemistry 33(23):7300-7308.
Campion et al. (1990) Biochemical Properties of Site-Directed Mutants of Human Epidermal Growth Factor: Importance of Solvent-Exposed Hydrophobic Residues of the Amino-Terminal Domain in Receptor Binding. Biochemistry 29(42):9988-9993.
Connolly (1983) Solvent-Accessible Surfaces of Proteins and Nucleic Acids. Science 221(4612):709-713.
Corrected Notice of Allowability corresponding to U.S. Appl. No. 11/656,646 dated Sep. 26, 2013.
Database Geneseq online Aug. 18, 2011 (Aug. 18, 2011)Heteromultimeric modified ubiquitin protein. SEQ ID 44., XP002756535, retrieved from EBI accession No. GSP:AZJ58575 Database accession No. AZJ58575.
Database Geneseq online Dec. 4, 2014 (Dec. 4, 2014)Anti-EGFR1 antibody light chain-TGF beta RII fusion protein, SEQ: 30., XP002756536, retrieved from EBI accession No. GSP:BBP24113 Database accession No. BBP24113.
Daugherty et al. (1998) Antibody affinity maturation using bacterial surface display. Protein Engineering 11(9):825-832.
De Kruif et al. (1995) Selection and Application of Human Single Chain Fv Antibody Fragments from a Semi-synthetic Phage Antibody Display Library with Designed CDR3 Regions. Journal of Molecular Biology 248:97-105.
Decision to grant corresponding to Russian Patent Application No. 2012115491/10(023353) dated Nov. 20, 2014.
Deed of Grant corresponding to Australian Patent No. 2010332932 dated May 2, 2013.
Deed of grant corresponding to Australian Patent No. 2010332938 dated Apr. 4, 2013.
Dikic et al. (2009) Ubiquitin-binding domains—from structures to functions. Nature Reviews 10:659-671.
Ebersbach et al. (2007) Affilin-Novel Binding Molecules Based on Human (-B-Crystallin, an All (-Sheet Protein. Journal of Molecular Biology 372:172-185.
Ecker et al. (1987) Gene Synthesis, Expression, Structures, and Functional Activities of Site-specific Mutants of Ubiquitin. The Journal of Biological Chemistry 262(29):14213-14221.
Ermolenko et al. (2003) Noncharged amino acid residues at the solvent-exposed positions in the middle and at the C terminus of the alpha-helix have the same helical propensity. Protein Science 12(6):1169-1176.
European Search Report corresponding to European Patent Application No. 06 118 519.5-2401 dated Apr. 2, 2007.
Fiedler et al. (2006) Affilintm Molecules: Novel Ligands for Bioseparation. Food and Bioproducts Processing. 84(C1):3-8.
Finucane et al. (1999a) Core-Directed Protein Design. I. An Experimental Method for Selecting Stable Proteins from Combinatorial Libraries. Biochemistry 38:11604-11612.
Finucane et al. (1999b) Core-Directed Protein Design. II. Rescue of a Multiply Mutated and Destabilized Variant of Ubiquitin. Biochemistry 38(36):11613-11623.
Friedman et al. (2009) Engineering and characterization of a bispecific HER2 X EGFR-binding affibody molecule. Biotechnology and applied biochemistry academic press US 54(2):121-131.
Gebauer & Skerra (2009) Engineered protein scaffolds as next-generation antibody therapeutics. Current Opinion in Chemical Biology 13(3):245-255.
Grabulovski et al. (2007) A Novel, Non-immunogenic Fyn SH3-derived Binding Protein with Tumor Vascular Targeting Properties. The Journal of Biological Chemistry 282(5):3196-3204.
Guo et al. (2004) Protein tolerance to random amino acid change. PNAS 101(25):9205-9210.
Hanes & Plückthun (1997) In vitro selection and evolution of functional proteins by using ribosome display. PNAS 94(10):4937-4942.

(56) References Cited

OTHER PUBLICATIONS

Hanes et al. (1998) Ribosome display efficiently selects and evolves high-affinity antibodies in vitro from immune libraries. PNAS 95:14130-14135.
Hanes et al. (2000) Picomolar affinity antibodies from a fully synthetic naive library selected and evolved by ribosome display. Nature Biotechnology 18:1287-1292.
He & Taussig (1997) Antibody-ribosome-mRNA (ARM) complexes as efficient selection particles for in vitro display and evoluation of antibody combining sites. Nucleic Acids Research 25(24):5132-5134.
Hershko & Ciechanover (1998) The Ubiquitin System. Annu Rev Biochem 67:425-479.
Hey et al. (2005) Artificial, non-antibody binding proteins for pharmaceutical and industrial application. Trends in Biotehcnology 23(10):514-522.
Humphrey et al. (1990) Anti-synthetic peptide antibody reacting at the fusion junction of deletion-mutant epidermal growth factor receptors in human glioblastoma. Proc Natl Acad Sci. 87:4207-4211.
International Preliminary Report on Patentability (Chapter I of the Patent Cooperation Treaty) corresponding to International Patent Application No. PCT/EP2016/052345 dated Aug. 8, 2017.
International Preliminary Report on Patentability (Chapter I of the Patent Cooperation Treaty) corresponding to International Patent Application No. PCT/EP2007/062375 dated May 19, 2009.
International Preliminary Report on Patentability (Chapter I of the Patent Cooperation Treaty) corresponding to International Patent Application No. PCT/EP2010/069665 dated Jun. 19, 2012.
International Preliminary Report on Patentability corresponding to International Patent Application No. PCT/EP2016/67216 dated Jan. 23, 2018.
International Search Report and Written Opinion corresponding to International Patent Application No. PCT/EP2016/052408 dated May 2, 2016.
International Search Report corresponding to International Patent Application No. PCT/EP2000/006698 dated Feb. 2, 2001.
International Search Report corresponding to International Patent Application No. PCT/EP2004/005730 dated Oct. 5, 2004.
International Search Report corresponding to International Patent Application No. PCT/EP2005/010932 dated Apr. 11, 2006.
International Search Report corresponding to International Patent Application No. PCT/EP2007/062375 dated Apr. 25, 2008.
International Search Report corresponding to International Patent Application No. PCT/EP2010/069665 dated Apr. 13, 2011.
International Search Report corresponding to International Patent Application No. PCT/EP2010/069674 dated Jun. 17, 2011.
International Search Report corresponding to International Patent Application No. PCT/EP2012/061455 dated Oct. 25, 2012.
International Search Report corresponding to International Patent Application No. PCT/EP2011/002962 dated Mar. 19, 2012.
International Search Report corresponding to International Patent Application No. PCT/EP2012/061459 dated Sep. 24, 2012.
International Search Report corresponding to International Patent Application No. PCT/EP2013/062310 dated Aug. 2, 2013.
International Search Report corresponding to International Application No. PCT/EP2016/067207 dated Sep. 29, 2016.
International Search Report and Written Opinion corresponding to International Application No. PCT/EP2016/067216 dated Oct. 12, 2016.
International Search Report and Written Opinion corresponding to International Application No. PCT/EP2016/066774 dated Sep. 14, 2016.
Interview Summary and Corrected Notice of Allowability corresponding to U.S. Appl. No. 11/283,332 dated Jul. 1, 2014.
Interview Summary and Corrected Notice of Allowability corresponding to U.S. Appl. No. 12/072,959, dated Jun. 27, 2014.
Interview Summary corresponding to U.S. Appl. No. 11/283,332 dated Dec. 13, 2013.
Jackson (2006) Ubiquitin: a small protein folding paradigm. Org Biomol Chem 4(10):1845-1853.
Khorasanizadeh et al. (1993) Folding and stability of a tryptophan-containing mutant of ubiquitin. Biochemistry 32(27):7054-7063.
Kiel & Serrano (2006) The Ubiquitin Domain Superfold: Structure-based Sequence Alignments and Characterization of Binding Epitopes. Journal of Molecular Biology 355(4):821-844.
Knappik et al. (2000) Fully Synthetic Human Combinatorial Antibody Libraries (HuCAL) Based on Modular Consensus Frameworks and CDRs Randomized with Trinucleotides. Journal of Molecular Biology 296:57-86.
Koide et al. (1998)The Fibronectin Type III Domain as a Scaffold for Novel Binding Proteins. Journal of Molecular Biology 284:1141-1151.
Kolchanov & Shindyalov (1988) Single amino acid substitutions producing instability of globular proteins. Calculation of their frequencies in the enitre mutational spectra of the alpha- and beta-subunits of human hemoglobin. Journal of Molecular Evolution 27:154-162.
Krantz et al. (2004) Discerning the Structure and Energy of Multiple Transition States in Protein Folding using $\Psi$-analysis. Journal of Molecular Biology 337(2):463-475.
Krippner-Heidenreich et al. (2008) Single-chain TNF, a TNF derivative with enhanced stability and antitumoral activity. Journal of Immunology 180:8176-8183.
Ku & Schultz (1995) Alternate protein frameworks for molecular recognition. PNAS 92:6552-6556.
Larsen & Wang. (2002) The Ubiquitin Superfamily: Members, Features, and Phylogenies. Journal of Proteome Research 1:411-419.
Laub et al. (1995) Localized solution structure refinement of an F45W variant of ubiquitin using stochastic boundary molecular dynamics and NMR distance restraints. Protein Science 4:973-982.
Lazar & Wang (1997) H.De novo design of the hydrophobic core of ubiquitin. Protein Science 6:1167-1178.
Lipovsek & Plückthun (2004) In-vitro protein evolution by ribosome display and mRNA display. Journal of Immunological Methods 290:51-67.
Lo et al. (2009) Structural Basis for Recognition of Diubiquitins by NEMO. Molecular Cell 33:602-615.
Loladze et al. (2005) Both helical propensity and side-chain hydrophobicity at a partially exposed site in alpha-helix contribute to the thermodynamic stability of ubiquitin. Proteins 58(1):1-6.
Lorey et al. (2014) Novel ubiquitin-derived high affinity binding proteins with tumor targeting properties. Journal of Biological Chemistry. 289(12):8493-8507.
Mayr et al. (1994) Domain Interactions and Connecting Peptides in Lens Cyrstallins. Journal of Molecular Biology 235:84-88.
McConnell & Hoess (1995) Tendamistat as a Scaffold for Conformationally Constrained Phage Peptide Libraries. The Journal of Molecular Biology 259:460-479.
Miura et al. (1999) Characterization of the Binding Interafce bewteen Ubiquitin and Class I Human Ubiquitin-conjugating Enzyme 2b by Multidimensional Heteronuclear NMR Spectroscopy in Solution Journal of Molecular Biology 290:213-228.
Müller & Skerra (1994) A.Grafting of a High-Affinity Zn(II)-Binding Site on the β-Barrel of Retional-Binding Protein Results in Enhanced Folding Stability and Enables Simplified Purification. Biochemistry 33(47):14126-14135.
Müller et al. (2001) SUMO, ubiquitin's mysterious cousin. Nat. Rev. Mol. Cell Biol. 2:202-210.
Notice of Allowance corresponding to U.S. Appl. No. 10/030,605 dated Apr. 14, 2009.
Notice of Allowance corresponding to U.S. Appl. No. 11/283,332, dated Jun. 6, 2014.
Notice of Allowance corresponding to U.S. Appl. No. 11/732,632 dated Aug. 23, 2010.
Notice of Allowance corresponding to U.S. Appl. No. 11/656,646, dated Aug. 27, 2013.
Notice of Allowance corresponding to U.S. Appl. No. 12/072,959 dated Jun. 3, 2014.
Notice of Allowance corresponding to U.S. Appl. No. 12/514,550 dated Sep. 10, 2013.

(56) References Cited

OTHER PUBLICATIONS

Notice of Allowance corresponding to U.S. Appl. No. 13/142,195, dated Aug. 4, 2014.
Notice of Allowance corresponding to U.S. Appl. No. 13/144,809 dated Mar. 3, 2014.
Notice of Allowance corresponding to U.S. Appl. No. 14/126,358 dated Sep. 9, 2016.
Notification Concerning Transmittal of International Preliminary Report on Patentability (Chapter I of the Patent Cooperation Treaty) corresponding to International Patent Application No. PCT/EP2016/052345 dated Apr. 11, 2016.
Notification Concerning Transmittal of International Preliminary Report on Patentability (Chapter I of the Patent Cooperation Treaty) corresponding to International Patent Application No. PCT/EP2010/069666 dated Jun. 28, 2012.
Notification Concerning Transmittal of International Preliminary Report on Patentability (Chapter I of the Patent Cooperation Treaty) corresponding to International Patent Application No. PCT/EP2010/069674 dated Jun. 28, 2012.
Notification Concerning Transmittal of International Preliminary Report on Patentability (Chapter I of the Patent Cooperation Treaty) corresponding to International Patent Application No. PCT/EP2004/005730 dated Apr. 13, 2006.
Notification Concerning Transmittal of International Preliminary Report on Patentability (Chapter I or Chapter II of the Patent Cooperation Treaty) corresponding to International Patent Application No. PCT/EP2005/010932 dated May 3, 2007.
Nygren & Uhlen (1997) Scaffolds for engineering novel binding sites in proteins. Current Opinion in Structural Biology 7:463-469.
Office Action corresponding to Australian Patent Application No. 2012268970 dated Aug. 27, 2015.
Office action corresponding to Canadian Patent Applicaiton No. 2,837,804 date May 1, 2015.
Office action corresponding to Canadian Patent Application No. 2,778,871 dated Jan. 30, 2014.
Office action corresponding to Chinese Patent Application No. 201080056911.6 dated Jul. 31, 2013. Translation.
Office action corresponding to European Patent Application No. EP 10 787 815.9-1410 dated Aug. 13, 2012.
Office action corresponding to Japanese Patent Application No. 2012-504036 dated Aug. 26, 2013.
Office action corresponding to Japanese Patent Application No. 2012-542583 dated Apr. 22, 2014.
Office action corresponding to Korean Patent Application No. 10-2011-7018847 dated Jan. 30, 2013. Translation.
Office action corresponding to Russian Patent Application No. 2012114662/10(022146) dated Sep. 8, 2014. (with Translation).
Office Action corresponding to Russian Patent Application No. 2012115491 dated Dec. 24, 2013.
Office Action corresponding to Russian Patent Application No. 2012114662/10(022146) dated Dec. 18, 2013.
Office Action corresponding to U.S. Appl. No. 12/072,959 dated Jan. 27, 2009.
Office Action corresponding to U.S. Appl. No. 10/030,605 dated Sep. 21, 2004.
Office Action corresponding to U.S. Appl. No. 10/030,605 dated Feb. 15, 2005.
Office Action corresponding to U.S. Appl. No. 10/030,605 dated Aug. 10, 2005.
Office Action corresponding to U.S. Appl. No. 10/030,605 dated Apr. 12, 2006.
Office Action corresponding to U.S. Appl. No. 10/030,605 dated Feb. 28, 2007.
Office Action corresponding to U.S. Appl. No. 10/030,605 dated Nov. 16, 2007.
Office Action corresponding to U.S. Appl. No. 11/656,646 dated Sep. 1, 2009.
Office Action corresponding to U.S. Appl. No. 11/656,646 dated May 25, 2010.
Office Action corresponding to U.S. Appl. No. 10/030,605 dated Jul. 1, 2008.
Office Action corresponding to U.S. Appl. No. 11/656,646 dated Nov. 13, 2009.
Office Action corresponding to U.S. Appl. No. 11/283,332 dated Jan. 9, 2008.
Office Action corresponding to U.S. Appl. No. 11/283,332 dated May 30, 2008.
Office Action corresponding to U.S. Appl. No. 11/283,332 dated Nov. 28, 2008.
Office Action corresponding to U.S. Appl. No. 11/283,332 dated Sep. 4, 2009.
Office Action corresponding to U.S. Appl. No. 11/283,332 dated Sep. 3, 2013.
Office Action corresponding to U.S. Appl. No. 12/072,959 dated Jul. 24, 2008.
Office Action corresponding to U.S. Appl. No. 12/072,959 dated Aug. 30, 2013.
Office Action corresponding to U.S. Appl. No. 11/283,332 dated Mar. 3, 2010.
Office Action corresponding to U.S. Appl. No. 12/072,959 dated Jan. 5, 2010.
Office Action corresponding to U.S. Appl. No. 11/732,632 dated Jun. 3, 2009.
Office Action corresponding to U.S. Appl. No. 11/732,632 dated Aug. 21, 2009.
Office Action corresponding to U.S. Appl. No. 11/732,632 dated Mar. 19, 2010.
Office Action corresponding to U.S. Appl. No. 12/514,550 dated Aug. 3, 2011.
Office Action corresponding to U.S. Appl. No. 12/514,550 dated Sep. 15, 2011.
Office Action corresponding to U.S. Appl. No. 12/514,550 dated Mar. 12, 2012.
Office Action corresponding to U.S. Appl. No. 13/142,195 dated Feb. 11, 2013.
Office Action corresponding to U.S. Appl. No. 13/142,195 dated May 29, 2013.
Office Action corresponding to U.S. Appl. No. 13/142,195 dated Feb. 4, 2014.
Office Action corresponding to U.S. Appl. No. 13/144,809 dated Oct. 18, 2013.
Office Action corresponding to U.S. Appl. No. 13/516,002 dated Jan. 26, 2015.
Office Action corresponding to U.S. Appl. No. 13/516,002 dated Apr. 6, 2015.
Office Action corresponding to U.S. Appl. No. 14/126,341 dated May 1, 2015.
Office Action corresponding to U.S. Appl. No. 14/126,341 dated Sep. 29, 2015.
Office Action corresponding to U.S. Appl. No. 14/126,358 dated Apr. 6, 2016.
Office Action corresponding to U.S. Appl. No. 14/407,213 dated May 25, 2016.
Office Action Restriction Requirement corresponding to U.S. Appl. No. 14/126,358 dated Oct. 28, 2015.
Office Action Restriction Requirement corresponding to U.S. Appl. No. 14/407,213 dated Jan. 21, 2016.
Ohashi et al. (2007) Efficient protein selection based on ribosome display system with purified components. Biochemical and Biophysical Research Communications 352:270-276.
Raasi Shahri et al. (2004) Binding of Polyubiquitin chains to ubiquitin-associated (UBA) domains of HHR23A. J. Mol. Biol. 34:1367-1379.
Rahighi et al. (2009) Specific Recognition of Linear Ubiquitin Chains by NEMO Is Important for NF-κB Activation. Cell 136:1098-1109.
Search Report corresponding to Chinese Patent Application No. 201080056911.6 dated Jun. 14, 2013. Translation.
Skerra (2000) Engineered protein scaffolds for molecular recognition. Journal of Molecular Recognition 13(4):167-187.
Skerra et al. (2007) Alternative non-antibody scaffolds for molecular recognition. Current Opinion in Biotechnology 18(4):295-304.

(56) References Cited

OTHER PUBLICATIONS

Smith et al. (1998) Small Binding Proteins Selected from a Conbinatorial Repertoire of Knottins Displayed on Phage. Journal of Molecular Biology 277(2):317-332.
Lorey et al. (2014) Novel Ubiquitin-derived High Affinity Binding Proteins with Tumor Targeting Properties. J of Bio Chem 289(12):8493-8507.
Ubiquitin-like Superfamily (2004) pp. 1-4.
Weidle et al. (2013) The Emerging Role of New Protein Scaffold-based Agents for Treament of Cancer. Caner Genomics & Proteomics 10(4):155-168.
Wells & Lowmann (1992).Rapid evolution of peptide and protein binding properties in vitro. Current Opinion in Biotechnology 3:355-362.
Wells (1990) Additivity of Mutational Effects in Proteins. Biochemistry 29(37):8509-8517.
Yeh et al. (2000) Ubiquitin-like proteins: new wines in new bottles. Gene 248(1-2):1-14.
Zahnd et al. (2007) Ribosome display: selecting and evolving proteins in vitro that specifically bind to a target. Nature Methods 4(3):269-279.
Zhang et al. (1997) Directed evolution of a fucosidase from a galactosidase by DNA shuffling and screening. PNAS 94:4504-4509.
Office Action (Restriction Requirement) corresponding to U.S. Appl. No. 15/549,022 dated May 3, 2018.
Office Action (Restriction Requirement) corresponding to U.S. Appl. No. 15/549,022, dated Nov. 8, 2018.
European Search Report corresponding to European Patent Application No. 09 176 574.3-2401 dated Jan. 18, 2010.
European Search Report corresponding to European Patent Application No. 10 181 802.9-2401 dated Feb. 10, 2011.
International Preliminary Report on Patentability corresponding to International Patent Application No. PCT/EP2004/005730 dated May 13, 2005.
Nord et al. (1997) Binding proteins selected from combinatorial libraries of an ☐-helical bacterial receptor domain. Nature Biotechnology 15:772-777.
Office Action corresponding to European Patent Application No. 00 944 034.8-2401 dated Oct. 7, 2004.
Office Action Restriction Requirement corresponding to U.S. Appl. No. 15/548,976 dated Jun. 14, 2019.
Office Action Restriction Requirement corresponding to U.S. Appl. No. 15/548,976 dated Sep. 9, 2019.
Pack & Pluckthun (1992) A.Miniantibodies: Use of Amphipathic Helices to Produce Functional, Flexibly Linked Dimeric Fv Fragments with High Avidity in *Escherichia coli*. Biochemsitry 31(6):1579-1584.

FIG. 3 A

| SEQ ID NO: | Affilin | R42 | I44 | H68 | V70 | R72 | L73 | R74 | K82 | L84 | Q138 | K139 | E140 | S141 | T142 |
|---|---|---|---|---|---|---|---|---|---|---|---|---|---|---|---|
| 5 | 142437 | T | A | W | Y | T | W | N | T | H | S | E | W | A | I |
| 6 | 142672 | T | A | W | Y | T | W | Y | L | D | R | G | W | . | L |
| 7 | 144637 | T | A | W | Y | T | W | Y | T | H | S | E | W | A | I |
| 8 | 144636 | T | A | W | Y | T | W | Y | T | H | S | E | W | A | I |
| 9 | 144635 | T | A | W | Y | T | W | Y | T | H | S | E | W | A | I |
| 10 | 144634 | T | A | W | Y | T | W | Y | T | H | S | E | W | A | I |
| 11 | 144633 | T | A | W | Y | T | W | Y | T | H | S | E | W | A | I |
| 12 | 144632 | T | A | W | Y | T | W | Y | T | H | S | E | W | A | I |
| 13 | 144631 | T | A | W | Y | T | W | Y | T | H | S | E | W | A | I |
| 14 | 142679 | T | A | W | Y | T | W | Y | T | H | S | E | W | A | I |
| 15 | 142658 | T | A | W | Y | T | W | Y | T | H | S | E | W | A | I |
| 16 | 142654 | T | A | W | Y | T | W | Y | T | H | S | E | W | A | I |
| 38 | 141884 | T | A | W | Y | T | W | Y | T | H | S | E | W | A | I |
| 17 | 142653 | T | A | W | Y | T | W | Y | T | H | S | E | W | A | I |
| 18 | 142645 | T | A | W | Y | T | W | Y | T | H | S | E | W | A | I |
| 19 | 142628 | T | A | W | Y | T | W | Y | T | H | S | E | W | A | I |
| 20 | 142620 | T | A | W | Y | T | W | Y | T | H | S | E | W | A | I |
| 21 | 142618 | T | A | W | Y | T | W | Y | T | H | S | E | W | A | I |
| 22 | 142617 | T | A | W | Y | T | W | Y | T | H | S | E | W | A | I |
| 23 | 142609 | T | A | W | Y | T | W | Y | T | H | S | E | W | A | I |
| 24 | 142451 | T | A | W | Y | T | W | Y | T | H | S | E | W | A | I |
| 25 | 142441 | T | A | W | Y | T | W | Y | T | H | S | E | W | A | I |
| 26 | 142439 | T | A | W | Y | T | W | Y | T | H | S | E | W | A | I |
| 27 | 141931 | T | A | W | Y | T | W | Y | T | H | S | E | W | A | I |
| 28 | 141926 | T | A | W | Y | T | W | Y | T | H | S | E | W | A | I |
| 29 | 141869 | T | A | W | Y | T | W | Y | T | H | S | E | W | A | I |
| 30 | 141890 | T | A | Y | Y | T | V | K | Y | H | E | L | W | R | N |
| 31 | 141912 | T | . | F | Y | Y | V | S | L | D | E | L | W | R | N |
| 32 | 141935 | T | T | Y | Y | G | I | S | I | S | E | L | W | R | N |
| 33 | 142465 | L | S | . | W | G | V | . | N | E | S | E | W | A | I |
| 34 | 142655 | S | V | Y | Y | F | S | . | L | D | R | G | W | . | L |
| 35 | 142418 | S | V | Y | Y | F | S | . | L | D | R | G | W | . | L |
| 36 | 142627 | S | V | Y | Y | F | S | . | L | D | S | E | W | A | I |
| 37 | 141975 | S | V | Y | Y | F | S | . | L | D | S | E | W | A | I |

FIG. 3 B

| SEQ ID NO: | Affilin- | 42 | 44 | 68 | 70 | 72 | 73 | 74 | 82 | 84 | 138 | 139 | 140 | 141 | 142 |
|---|---|---|---|---|---|---|---|---|---|---|---|---|---|---|---|
| 5 | 142437 | ~ | H | O | O | ~ | O | ~ | ~ | + | ~ | - | O | H | H |
| 6 | 142672 | ~ | H | O | O | ~ | O | O | H | - | + | G | O | ~ | H |
| 7 | 144637 | ~ | H | O | O | ~ | O | O | ~ | + | ~ | - | O | H | H |
| 8 | 144636 | ~ | H | O | O | ~ | O | O | ~ | + | ~ | - | O | H | H |
| 9 | 144635 | ~ | H | O | O | ~ | O | O | ~ | + | ~ | - | O | H | H |
| 10 | 144634 | ~ | H | O | O | ~ | O | O | ~ | + | ~ | - | O | H | H |
| 11 | 144633 | ~ | H | O | O | ~ | O | O | ~ | + | ~ | - | O | H | H |
| 12 | 144632 | ~ | H | O | O | ~ | O | O | ~ | + | ~ | - | O | H | H |
| 13 | 144631 | ~ | H | O | O | ~ | O | O | ~ | + | ~ | - | O | H | H |
| 14 | 142679 | ~ | H | O | O | ~ | O | O | ~ | + | ~ | - | O | H | H |
| 15 | 142658 | ~ | H | O | O | ~ | O | O | ~ | + | ~ | - | O | H | H |
| 16 | 142654 | ~ | H | O | O | ~ | O | O | ~ | + | ~ | - | O | H | H |
| 38 | 141884 | ~ | H | O | O | ~ | O | O | ~ | + | ~ | - | O | H | H |
| 17 | 142653 | ~ | H | O | O | ~ | O | O | ~ | + | ~ | - | O | H | H |
| 18 | 142645 | ~ | H | O | O | ~ | O | O | ~ | + | ~ | - | O | H | H |
| 19 | 142628 | ~ | H | O | O | ~ | O | O | ~ | + | ~ | - | O | H | H |
| 20 | 142620 | ~ | H | O | O | ~ | O | O | ~ | + | ~ | - | O | H | H |
| 21 | 142618 | ~ | H | O | O | ~ | O | O | ~ | + | ~ | - | O | H | H |
| 22 | 142617 | ~ | H | O | O | ~ | O | O | ~ | + | ~ | - | O | H | H |
| 23 | 142609 | ~ | H | O | O | ~ | O | O | ~ | + | ~ | - | O | H | H |
| 24 | 142451 | ~ | H | O | O | ~ | O | O | ~ | + | ~ | - | O | H | H |
| 25 | 142441 | ~ | H | O | O | ~ | O | O | ~ | + | ~ | - | O | H | H |
| 26 | 142439 | ~ | H | O | O | ~ | O | O | ~ | + | ~ | - | O | H | H |
| 27 | 141931 | ~ | H | O | O | ~ | O | O | ~ | + | ~ | - | O | H | H |
| 28 | 141926 | ~ | H | O | O | ~ | O | O | ~ | + | ~ | - | O | H | H |
| 29 | 141869 | ~ | H | O | O | ~ | O | O | ~ | + | ~ | - | O | H | H |
| 30 | 141890 | ~ | H | O | O | ~ | H | + | O | + | - | H | O | + | ~ |
| 31 | 141912 | ~ | H | O | O | O | H | ~ | H | - | - | H | O | + | ~ |
| 32 | 141935 | ~ | ~ | O | O | G | H | ~ | H | ~ | - | H | O | + | ~ |
| 33 | 142465 | H | ~ | + | O | G | H | + | ~ | - | ~ | - | O | H | H |
| 34 | 142655 | ~ | H | O | O | O | ~ | + | H | - | + | G | O | ~ | H |
| 35 | 142418 | ~ | H | O | O | O | ~ | + | H | - | + | G | O | ~ | H |
| 36 | 142627 | ~ | H | O | O | O | ~ | + | H | - | ~ | - | O | H | H |
| 37 | 141975 | ~ | H | O | O | O | ~ | + | H | - | ~ | - | O | H | H |

FIG. 3 C

| SEQ | Affilin- | K 6 | G 10 | K 11 | L 15 | S 20 | D 21 | I 23 | K 27 | A 28 | Q 31 | E 34 | I 36 | Q 40 | A 46 | K 48 | Q 49 | D 52 | D 58 | Q 62 | K 63 | A 75 | Q 78 | T 88 | E 92 | P 95 | S 96 | T 98 | P 114 | I 120 | K 124 | T 131 | S 133 | H 144 | L 147 |
|---|---|---|---|---|---|---|---|---|---|---|---|---|---|---|---|---|---|---|---|---|---|---|---|---|---|---|---|---|---|---|---|---|---|---|---|
| 5 | 142437 | . | . | . | . | . | N | . | . | . | . | . | T | . | . | . | H | . | . | . | . | . | R | N | . | . | . | . | . | . | . | . | . | . | . |
| 6 | 142672 | . | . | . | . | . | . | . | . | . | . | . | . | . | T | . | . | . | . | . | . | . | R | . | . | . | . | . | . | . | . | . | . | . | . |
| 7 | 144637 | . | . | . | . | . | . | T | . | . | . | . | . | . | V | . | . | Y | . | . | . | . | R | . | D | . | . | . | . | . | . | . | . | . | . |
| 8 | 144636 | . | . | . | . | . | . | T | . | . | . | . | . | . | V | . | . | Y | . | . | . | . | R | . | . | . | . | . | . | . | . | . | . | . | . |
| 9 | 144635 | . | . | . | . | . | . | . | . | . | . | . | . | . | V | M | . | . | . | . | . | . | R | . | D | . | . | . | . | . | M | . | . | . | . |
| 10 | 144634 | . | . | . | . | . | . | . | . | . | . | . | . | . | V | . | . | . | . | . | . | . | R | . | D | . | . | . | . | . | M | . | . | . | . |
| 11 | 144633 | . | . | . | . | . | . | . | . | . | . | . | . | . | V | . | . | Y | . | . | . | . | R | . | D | . | . | . | . | . | . | . | . | . | . |
| 12 | 144632 | . | . | . | . | . | . | T | . | . | . | . | . | . | V | . | . | . | . | . | . | . | R | . | . | . | . | . | . | . | . | . | . | . | . |
| 13 | 144631 | . | . | . | . | . | . | . | . | . | . | . | . | . | V | . | . | . | . | . | . | . | R | . | D | . | . | . | . | . | . | . | . | . | . |
| 14 | 142679 | R | . | . | . | . | . | . | . | . | . | . | . | . | V | . | . | . | . | . | . | . | R | . | . | . | . | . | . | . | . | . | . | . | . |
| 15 | 142658 | . | . | . | . | . | . | . | . | . | . | . | T | . | . | . | . | . | . | . | . | . | R | . | . | . | . | . | . | . | . | . | . | Q | . |
| 16 | 142654 | . | . | . | . | . | . | . | . | . | . | . | . | . | V | . | . | . | . | . | . | . | R | . | . | . | . | . | . | . | . | . | . | . | . |
| 38 | 141884 | . | . | . | . | . | . | R | . | . | . | . | . | . | . | . | . | . | . | . | . | . | R | . | . | . | . | . | . | . | . | . | . | . | . |
| 17 | 142653 | . | . | . | . | . | . | . | . | . | . | . | . | . | V | . | . | . | . | . | . | . | R | . | . | . | S | . | . | . | . | . | . | . | . |
| 18 | 142645 | . | D | . | . | . | . | . | . | . | . | . | . | . | . | . | . | . | . | . | . | . | R | . | . | . | . | . | . | . | . | . | T | . | . |
| 19 | 142628 | . | . | . | . | . | . | T | . | . | . | . | . | . | V | . | . | . | . | . | . | . | R | . | D | . | . | . | . | . | . | . | . | . | . |
| 20 | 142620 | . | . | . | . | . | . | . | . | V | . | . | . | . | V | . | . | . | . | . | . | . | R | . | . | . | . | . | . | . | . | . | . | . | . |
| 21 | 142618 | . | . | . | . | . | . | . | . | . | . | . | . | K | V | . | . | . | . | . | . | . | . | . | . | . | . | . | . | . | . | . | . | . | . |
| 22 | 142617 | . | . | . | . | . | . | . | . | . | . | . | . | . | V | . | . | . | . | . | . | . | R | . | . | . | S | . | . | . | A | . | . | . | . |
| 23 | 142609 | . | . | N | . | . | . | . | . | . | . | . | . | . | V | . | . | . | . | . | . | . | R | . | . | . | . | . | . | . | . | . | . | . | P |
| 24 | 142451 | . | . | . | . | . | . | . | . | . | . | . | . | . | V | . | . | . | . | . | . | . | R | . | . | T | . | . | N | . | . | . | . | . | . |
| 25 | 142441 | . | N | . | . | . | . | . | . | . | . | . | . | . | . | . | . | . | . | . | . | . | R | . | . | . | . | . | . | . | . | . | . | . | . |
| 26 | 142439 | . | . | . | . | . | . | . | . | . | . | . | . | . | . | . | . | Y | . | . | . | . | R | . | . | . | . | . | . | . | . | . | . | . | . |
| 27 | 141931 | . | . | . | . | . | . | . | . | . | . | . | . | . | V | . | . | . | . | . | . | . | . | . | . | . | . | . | . | . | . | . | . | . | . |
| 28 | 141926 | . | . | . | . | . | . | . | . | . | . | . | . | . | . | . | . | . | . | . | . | . | R | . | . | . | . | . | . | . | . | . | . | . | . |
| 29 | 141869 | . | . | . | . | . | . | . | . | . | . | . | . | . | . | . | . | . | . | . | . | . | . | . | . | . | . | . | . | . | . | . | . | . | . |
| 30 | 141890 | R | . | . | . | . | . | . | . | . | . | . | . | . | V | . | . | . | . | R | . | . | . | . | . | . | . | . | . | . | . | . | . | . | . |
| 31 | 141912 | . | . | . | . | . | . | . | . | . | V | . | . | . | . | . | . | . | . | . | . | . | . | . | . | . | . | . | . | . | . | . | . | . | . |
| 32 | 141935 | . | . | . | . | . | . | . | . | . | . | D | . | . | . | . | . | . | . | . | . | . | . | . | . | . | . | . | . | . | . | . | . | . | . |
| 33 | 142465 | . | . | . | . | . | . | . | . | . | . | . | . | . | . | . | . | . | . | . | . | . | . | . | . | . | . | . | . | . | . | . | . | . | . |
| 34 | 142655 | . | . | . | . | . | . | . | L | . | . | . | . | . | . | . | . | V | . | . | . | . | R | . | . | . | S | . | . | . | . | . | . | . | . |
| 35 | 142418 | . | . | . | . | . | . | . | . | . | . | . | . | . | . | . | . | . | . | . | I | . | R | . | . | . | . | . | . | . | . | . | . | . | . |
| 36 | 142627 | . | . | . | V | C | . | . | . | . | . | . | . | . | . | . | . | . | . | . | . | . | R | . | . | . | . | . | . | . | . | . | . | . | . |
| 37 | 141975 | . | . | . | . | . | . | . | . | . | . | . | . | . | . | . | . | Y | . | . | . | V | R | . | . | . | . | N | . | S | . | A | . | . | . |

FIG. 3 D

| | | + | G | + | H | ~ | H | + | H | ~ | H | ~ | H | + | ~ | ~ | + | H | ~ | ~ | P | ~ | ~ | P | H | + | ~ | ~ | + | H |
|---|---|---|---|---|---|---|---|---|---|---|---|---|---|---|---|---|---|---|---|---|---|---|---|---|---|---|---|---|---|---|
| No. | Afflin | 6 | 10 | 11 | 15 | 20 | 23 | 27 | 28 | 31 | 36 | 40 | 46 | 48 | 49 | 62 | 63 | 75 | 78 | 88 | 95 | 96 | 98 | 114 | 120 | 124 | 131 | 133 | 144 | 147 |
| 5 | 142437 | . | . | . | . | . | . | . | . | ~ | . | . | . | + | . | . | . | . | + | ~ | . | . | . | . | . | . | . | . | . | . |
| 6 | 142672 | . | . | . | . | . | . | . | . | . | . | . | ~ | . | . | . | . | . | + | . | . | . | . | . | . | . | . | . | . | . |
| 7 | 144637 | . | . | . | . | . | ~ | . | . | . | . | . | H | . | . | . | . | . | + | . | . | . | . | . | . | . | . | . | . | . |
| 8 | 144636 | . | . | . | . | . | ~ | . | . | . | . | . | H | . | . | . | . | . | + | . | . | . | . | . | . | . | . | . | . | . |
| 9 | 144635 | . | . | . | . | . | . | . | . | . | . | . | H | H | . | . | . | . | + | . | . | . | . | . | . | . | H | . | . | . | . |
| 10 | 144634 | . | . | . | . | . | . | . | . | . | . | . | H | . | . | . | . | . | + | . | . | . | . | . | . | . | H | . | . | . | . |
| 11 | 144633 | . | . | . | . | . | . | . | . | . | . | . | H | . | . | . | . | . | + | . | . | . | . | . | . | . | . | . | . | . | . |
| 12 | 144632 | . | . | . | . | . | ~ | . | . | . | . | . | H | . | . | . | . | . | + | . | . | . | . | . | . | . | . | . | . | . | . |
| 13 | 144631 | . | . | . | . | . | . | . | . | . | . | . | H | . | . | . | . | . | + | . | . | . | . | . | . | . | . | . | . | . | . |
| 14 | 142679 | + | . | . | . | . | . | . | . | . | . | . | H | . | . | . | . | . | + | . | . | . | . | . | . | . | . | . | . | . | . |
| 15 | 142658 | . | . | . | . | . | . | . | . | . | . | . | ~ | . | . | . | . | . | + | . | . | . | . | . | . | . | . | . | . | ~ | . |
| 16 | 142654 | . | . | . | . | . | . | . | . | . | . | . | H | . | . | . | . | . | + | . | . | . | . | . | . | . | . | . | . | . | . |
| 38 | 141884 | . | . | . | . | . | . | + | . | . | . | . | . | . | . | . | . | . | + | . | . | . | . | . | . | . | . | . | . | . | . |
| 17 | 142653 | . | . | . | . | . | . | . | . | . | . | . | H | . | . | . | . | . | + | . | . | . | ~ | . | . | . | . | . | . | . | . |
| 18 | 142645 | . | - | . | . | . | . | . | . | . | . | . | . | . | . | . | . | . | + | . | . | . | . | . | . | . | . | . | . | ~ | . |
| 19 | 142628 | . | . | . | . | . | ~ | . | . | . | . | . | H | . | . | . | . | . | + | . | . | . | . | . | . | . | . | . | . | . | . |
| 20 | 142620 | . | . | . | . | . | . | . | H | . | . | . | H | . | . | . | . | . | + | . | . | . | . | . | . | . | . | . | . | . | . |
| 21 | 142618 | . | . | . | . | . | . | . | . | . | . | + | H | . | . | . | . | . | . | . | . | . | . | . | . | . | . | . | . | . | . |
| 22 | 142617 | . | . | . | . | . | . | . | . | . | . | . | H | . | . | . | . | . | + | . | . | . | . | ~ | . | . | . | H | . | . | . |
| 23 | 142609 | . | . | ~ | . | . | . | . | . | . | . | . | H | . | . | . | . | . | + | . | . | . | . | . | . | . | . | . | . | . | P |
| 24 | 142451 | . | . | . | . | . | . | . | . | . | . | . | H | . | . | . | . | . | + | . | . | ~ | . | . | . | ~ | . | . | . | . | . |
| 25 | 142441 | . | ~ | . | . | . | . | . | . | . | . | . | . | . | . | . | . | . | + | . | . | . | . | . | . | . | . | . | . | . | . |
| 26 | 142439 | . | . | . | . | . | . | . | . | . | . | . | . | . | . | . | . | . | + | . | . | . | . | . | . | . | . | . | . | . | . |
| 27 | 141931 | . | . | . | . | . | . | . | . | . | . | . | H | . | . | . | . | . | . | . | . | . | . | . | . | . | . | . | . | . | . |
| 28 | 141926 | . | . | . | . | . | . | . | . | . | . | . | . | . | . | . | . | . | + | . | . | . | . | . | . | . | . | . | . | . | . |
| 29 | 141869 | . | . | . | . | . | . | . | . | . | . | . | . | . | . | . | . | . | . | . | . | . | . | . | . | . | . | . | . | . | . |
| 30 | 141890 | + | . | . | . | . | . | . | . | . | . | . | H | . | . | + | . | . | . | . | . | . | . | . | . | . | . | . | . | . | . |
| 31 | 141912 | . | . | . | . | . | . | . | . | . | H | . | . | . | . | . | . | . | . | . | . | . | . | . | . | . | . | . | . | . | . |
| 32 | 141935 | . | . | . | . | . | . | . | . | . | . | . | . | . | . | . | . | . | . | . | . | . | . | . | . | . | . | . | . | . | . |
| 33 | 142465 | . | . | . | . | . | . | . | . | . | . | . | . | . | . | . | . | . | . | . | . | . | . | . | . | . | . | . | . | . | . |
| 34 | 142655 | . | . | . | . | . | . | . | H | . | . | . | . | . | . | . | . | . | + | . | ~ | . | . | . | . | . | . | . | . | . | . |
| 35 | 142418 | . | . | . | . | . | . | . | . | . | . | . | . | . | . | . | H | . | + | . | . | . | . | . | . | . | . | . | . | . | . |
| 36 | 142627 | . | . | . | H | C | . | . | . | . | . | . | . | . | . | . | . | . | + | . | . | . | . | . | . | . | . | . | . | . | . |
| 37 | 141975 | . | . | . | . | . | . | . | . | . | . | . | . | . | . | . | . | H | + | . | . | ~ | . | ~ | . | . | H | . | . | . | . |

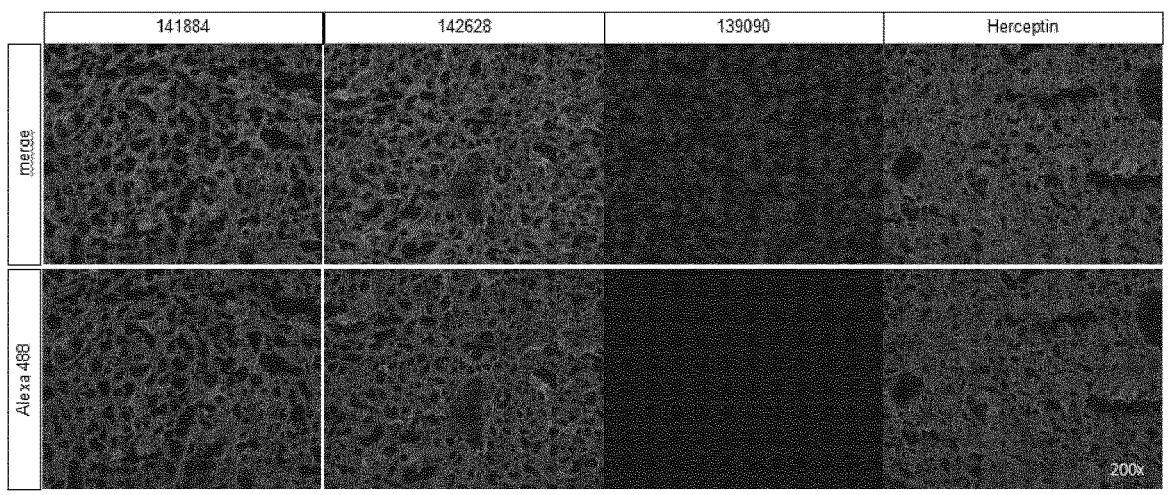
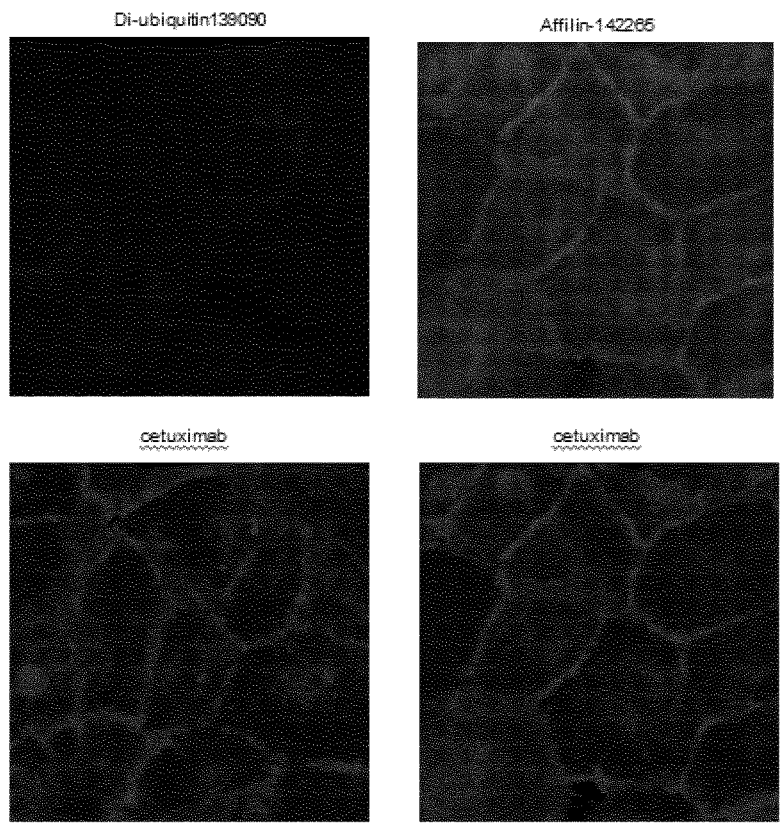

US 10,584,152 B2

BINDING PROTEINS BASED ON DI-UBIQUITIN MUTEINS AND METHODS FOR GENERATION

FIELD OF THE INVENTION

The present invention refers to new binding proteins based on di-ubiquitin modified in 12, 13, or 14 positions selected from R42, I44, H68, V70, R72, L73, R74, K82, L84, Q138, K139, E140, S141, and T142 and being able to bind specifically with high affinity to selected targets. The binding protein is based on two ubiquitin muteins moieties directly linked without any linker. Furthermore, the invention provides a method for the generation of said binding proteins. In addition, libraries encoding for said binding proteins based on di-ubiquitin muteins with modifications in 12, 13, or 14 positions selected from R42, I44, H68, V70, R72, L73, R74, K82, L84, Q138, K139, E140, S141, and T142 are provided.

BACKGROUND OF THE INVENTION

Non-immunoglobulin based binding agents can be beneficially used in the medical fields of diagnosis, prophylaxis and treatment of diseases. A solution to the disadvantages resulting from antibodies in diagnosis, prophylaxis and treatment of diseases is to provide polypeptides with comparable or even better affinity and specificity towards the specific targets combined with smaller molecular size enabling an improved tissue penetration and thus having better biodistribution properties.

Among non-immunoglobulin-derived small proteins, molecules based on modified ubiquitin are particularly interesting because these molecules promise alternative therapeutic and diagnostic possibilities compared to antibodies. Ubiquitin is a highly conserved, small, single domain protein present in all known eukaryotic cells and is 100% conserved amongst all vertebrates. In addition, ubiquitin naturally occurs in serum lowering the immunogenic potential. This facilitates preclinical development in different species required for toxicological and efficacy studies.

Target-specific ubiquitin muteins are known as Affilin® (registered trademark of Scil Proteins GmbH) proteins (see, for example, EP1626985B1, EP2379581B1, EP2094845B1, and WO2012/172055). Affilin proteins are engineered to generate de novo binding affinity towards desired targets making them ideal for applications that demand targeting and capturing of biomolecules. In addition, Affilin-based molecules can be conjugated with other functional molecules for targeting approaches as well as chemical coupling for half-life modulation (see, e.g. WO2012/172058, WO2014/094799).

It is an objective of the present invention to provide novel binding proteins and methods for the generation and identification of di-ubiquitin muteins with high binding capabilities to a target. It is a further object of the present invention to provide libraries for the identification of novel binding proteins based on di-ubiquitin muteins.

The above-described objectives and advantages are achieved by the subject-matters of the enclosed independent claims. Preferred embodiments of the invention are included in the dependent claims as well as in the following description, examples and figures. The above overview does not necessarily describe all problems solved by the present invention.

SUMMARY OF THE INVENTION

An aspect of the invention relates to a method for the generation of a binding protein which binds to a given target, preferably a protein or peptide or domain of a protein, with a dissociation constant ($K_D$) of at least 1000 nM, said method comprising subjecting nucleotide triplets of a nucleic acid molecule of di-ubiquitin (SEQ ID NO: 4) to mutagenesis in at least 12, 13, or 14 positions coding for amino acid positions R42, I44, H68, V70, R72, L73, R74, K82, L84, Q138, K139, E140, S141, and T142 of the linear polypeptide sequence of di-ubiquitin, resulting in one or more di-ubiquitin mutein nucleic acid molecule(s), expressing the one or more di-ubiquitin mutein nucleic acid molecule(s) obtained in (b) in a suitable expression system, enriching the one or more di-ubiquitin mutein(s) having a dissociation constant ($K_D$) of at least 1000 nM for a given target by means of selection and/or isolation, wherein said binding protein has between 85% and 92% sequence identity to di-ubiquitin (SEQ ID NO: 4), and wherein the affinity to the target is at least 10 fold higher than for di-ubiquitin.

A further aspect relates to a nucleic acid library encoding muteins of di-ubiquitin, wherein the amino acid residues selected from 12, 13, or 14 positions of sequence positions R42, I44, H68, V70, R72, L73, R74, K82, L84, Q138, K139, E140, S141, and T142 of di-ubiquitin are substituted in the muteins.

Another aspect relates to a method for identifying a binding protein with the affinity to the target of at least 10 fold higher than for di-ubiquitin comprising screening said library to identify a polypeptide that binds to a given target. In another aspect, the present invention relates to a binding protein with an affinity to a target comprising an amino acid sequence wherein at least 12, 13, or 14 amino acids selected from positions R42, I44, H68, V70, R72, L73, R74, K82, L84, Q138, K139, E140, S141, and T142 of di-ubiquitin (for example, SEQ ID NO: 4 or SEQ ID NO: 43) are substituted and wherein the binding protein has between 85% and 92% sequence identity to di-ubiquitin (for example, SEQ ID NO: 4 or a sequence with at least 95% identity, such as SEQ ID NO: 43) and wherein the affinity to the target is at least 10 fold higher than for di-ubiquitin (for example, SEQ ID NO: 4 or a sequence with at least 95% identity, such as SEQ ID NO: 43). The binding protein optionally comprises 1, 2, 3, 4, 5, or 6 further amino acid substitutions of di-ubiquitin. Further the binding protein may have a specific binding affinity ($K_D$) of at least 1000 nM, preferably at least 500 nM, preferably at least 100 nM, preferably at least 10 nM, to a target, preferably a peptide, a protein, or a domain of a protein, wherein the affinity to said target is at least 10 fold higher than for di-ubiquitin.

In a further aspect the present invention relates to a binding protein comprising at least one additional molecule, preferably selected from at least one member of the groups (i), (ii) and (iii) consisting of (i) a pharmacokinetic moiety modulating pharmacokinetic behavior selected from a polyethylene glycol (PEG), a human serum albumin (HSA), an albumin-binding peptide, or an immunoglobulin or immunoglobulin fragments, a polysaccharide, and, (II) a therapeutically active component, optionally selected from a monoclonal antibody or a fragment, cytokine, a chemokine, a cytotoxic compound, an enzyme, or derivatives thereof, or a radionuclide, and (iii) a diagnostic component, optionally selected from a fluorescent compound, a photosensitizer, a tag, an enzyme, or a radionuclide.

The present invention also provides, in further aspects, a nucleic acid or nucleic acids encoding the binding protein comprising or essentially consisting of a mutein of the present invention, as well as a vector or vectors comprising said nucleic acid or nucleic acids, and a host cell or host cells comprising said vector or vectors.

This summary of the invention does not necessarily describe all features of the present invention. Other embodiments will become apparent from a review of the ensuing detailed description.

BRIEF DESCRIPTION OF THE FIGURES

The Figures show:

FIG. 2 A compares the solubility of proteins encoded by five different libraries based on di-ubiquitin muteins directly connected (i.e. without a peptide linker between two ubiquitin moieties) (referred to as SPIF, SPKK, SPGO, SPOO) or joined via a peptide linker (SPVF). Libraries SPIF, SPKK, SPGO, and SPOO have at least 14 randomized positions starting between positions 42-74 and 122-142 of di-ubiquitin (SEQ ID NO: 4; see Examples for more details), except SPVF (randomized at positions 6-8, 62-66 at both ubiquitin moieties (SEQ ID NO: 1) linked via an amino-acid peptide linker). The columns show the values for more than 70% solubility of proteins encoded by the library. Surprisingly, the proteins encoded by SPIF library are highly soluble compared to all other libraries tested. The level of aggregation of proteins is very low (SPIF) compared to proteins encoded by other libraries.

FIG. 2 B compares the expression of the proteins encoded by the five different libraries mentioned above. Surprisingly, the proteins encoded by SPIF library show strong total expression values.

FIG. 3 shows binding molecules of the invention.

FIG. 3 A lists positions of di-ubiquitin (SEQ ID NO: 4) that are substituted in order to generate a Her2 binding protein. In the first row, the corresponding amino acid position is given. All Her2 binding proteins (for example, SEQ ID NOs: 5-38) are modified at least in 12, 13, or 14 positions selected from positions R42, I44, H68, V70, R72, L73, R74, K82, L84, Q138, K139, E140, S141, and T142 of SEQ ID NO: 4. A "." in the table refers to a wildtype position (unchanged); for example, in SEQ ID Nos: 6, 31, 33, 34, 35, 36, 37.

FIG. 3 B shows the same amino acid exchanges as FIG. 3 A, however, the exchanges are translated according to the following code which groups amino acids with similar biophysical properties. A waved line "–" is the symbol for polar amino acids (T, S, N, or Q) "H" is the symbol for hydrophobic amino acids (e.g. A, M, L, V, I) "O" is the symbol for aromatic amino acids (e.g. F, W, Y), "+" the symbol for basic amino acids (e.g. K, R, H), "−" the symbol for acidic amino acids (e.g. D, E), and "G" corresponds to Glycine.

FIG. 3 C. Further modifications are listed; all Her2 binding proteins have 0, 1, 2, 3, 4, 5, or 6 further modifications in addition to at least 12 positions selected from positions 42, 44, 68, 70, 72, 73, 74, 82, 84, 138, 139, 140, 141, and 142 of SEQ ID NO: 4.

FIG. 3 D shows the same amino acid exchanges as FIG. 3 C, however, the exchanges are translated according to the code which groups amino acids with similar biophysical properties as described in FIG. 3 B.

FIG. 4 A shows the binding kinetics of Affilin-142628 to Her2. Concentrations: 0 nM, 0.14 nM, 0.41 nM, 1.23 nM, 3.70 nM, 11.11 nM, and 33.33 nM.

FIG. 4 B shows the binding kinetics of Affilin-143488 to EpCAM. Concentrations were: Long dash (15.6 nM), medium dash (31.25 nM), short dash (6.5 nM), dotted (125 nM), dash dot (250 nM), dash dot dot (500 nM) and medium medium (1000 nM). Following a 1:1 binding mode (Langmuir) a $K_D$ of 150 nM vs epCAM was determined.

FIG. 4 C shows the binding kinetics of Affilin-143283 to EpCAM Concentrations were: Long dash (3.13 nM), medium dash (6.25 nM), solid (12.5 nM), short dash (25 nM), dotted (50 nM), dash dot (100 nM) and dash dot dot (200 nM). Following a 1:1 binding mode (Langmuir) a $K_D$ of 32 nM vs epCAM was determined.

FIG. 4 D shows the binding kinetics of Affilin-144160 to CD3. Concentrations were: Long dash (2 nM), medium dash (4 nM), short dash (8 nM), dotted (16 nM), dash dot (32 nM), dash dot dot (64 nM), medium medium (125 nM), short short short (250 nM) and short short (500 nM). Following a 1:1 binding mode (Langmuir) a $K_D$ of 46 nM vs CD3 was determined.

FIG. 5 A shows the affinity of Affilin-142265 to EGFR. The figure shows binding of Affilin-142265 (dark grey; black line) to exogenously EGFR expressing CHO-K1 cells (light grey) as determined by FACS analysis.

FIG. 5 B shows the high affinity of Her2 binding proteins to exogenously Her2 expressing CHO K1 cells at concentrations of 50 nM, 5 nM, and 0.5 nM. No binding was observed for di-ubiquitin or on control cells (empty vector control cells) FIG. 5 C shows the affinity of Her2 binding proteins to exogenously Her2 expressing SkBr cells as determined by FACS analysis. Cellular Her2 binding at 50 nM was confirmed for Affilin-proteins. No binding was observed to non-expressing HEK/293 control cells cells or for di-ubiquitin (139090).

FIG. 7. Binding analysis of Her2 binding proteins on SKOV-3 xenograft tumor tissue cells (immunohistological staining). The figure confirms that Her2 binding proteins bind to SKOV-3 tumor tissue whereas di-ubiquitin 139090 shows no binding on SKOV-3 tissue.

FIG. 8 confirms that Affilin proteins bind to extracellular EGFR expressed on tumor cells. Shown are immunofluorescence images of EGFR expressing A431 tumor cells. The staining of A431 tumor cells expressing EGFR confirms binding of Affilin-142265 whereas di-ubiquitin (139090) shows no binding.

DETAILED DESCRIPTION OF THE INVENTION

Figure 1:
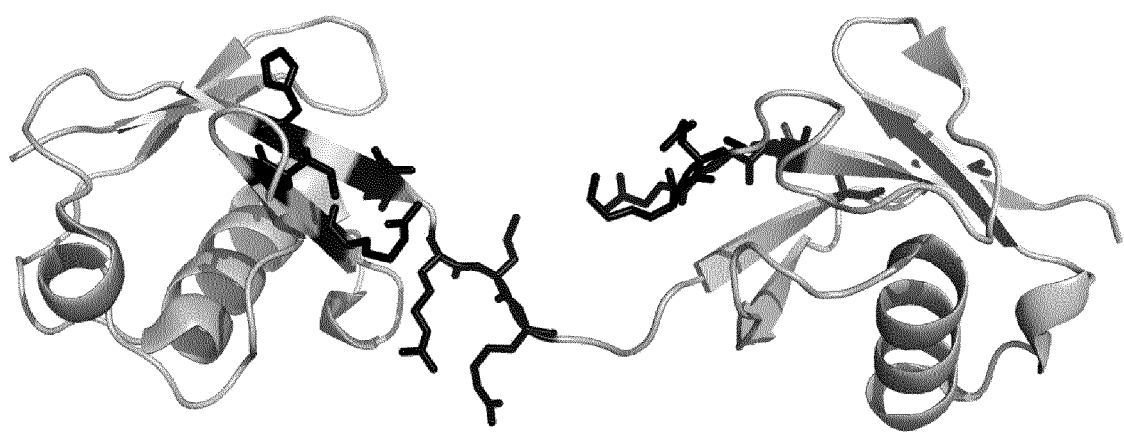
FIG. 1. Model of di-ubiquitin. Amino acid residues selected for generation of the SPIF library are shown in black.

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variants such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, GenBank Accession Number sequence submissions etc.) are cited throughout the text of this application. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, is a part of this specification.

Definitions of Important Terms Used in the Application

The terms "protein" and "polypeptide" refer to any chain of two or more amino acids linked by peptide bonds, and does not refer to a specific length of the product. Thus, "peptides", "protein", "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modifications by non-naturally occurring amino acids and similar modifications which are well known in the art. Thus, binding proteins comprising two or more protein moieties also fall under the definition of the term "protein" or "polypeptides". The term "binding protein" as used herein refers to a protein which either comprises or essentially consists of or consists of two ubiquitin muteins (Affilin) with specific binding affinity ($K_D$) of at least 1000 nM, preferably at least 500 nM, preferably at least 100 nM, preferably at least 10 nM, for example, when determined by surface plasmon resonance, to a target wherein the affinity to the target is at least 10 fold higher than for di-ubiquitin (for example, SEQ ID NO: 4 or at least 95% identical sequences such as SEQ ID NO: 43).

The terms "protein capable of binding" or "binding protein" or "binding affinity for" according to this invention refer to a protein comprising a binding capability to a defined target. The term "Her2 binding protein" refers to a protein with high affinity binding capability to Her2, the term "EGFR binding protein" refers to a protein with high affinity binding capability to EGFR, the term "CD3 binding protein" refers to a protein with high affinity binding capability to CD3, and the term "epCAM binding protein" refers to a protein with high affinity binding capability to epCAM.

In the present specification, the terms "target", "antigen", "target antigen", and "binding partner" are all used synonymously and can be exchanged. Preferably the target is one of the targets defined herein below. The term "antigen", as used herein, is to be interpreted in a broad sense and includes any target moiety that is bound by the binding moieties of the binding proteins of the present invention. Targets can be inorganic or organic substances. The term includes, for example, small molecules in body fluid such as drugs, toxins, autoantibodies, autoantigens, proteins, polypeptides, carbohydrates, nucleic acids and other molecules. Specific examples are a cancer target antigen, a receptor target antigen on immune cells, and a soluble target antigen selected e.g. from hormones, and cytokines. Summarizing, as target antigen according to the invention all biologically and medically active and relevant molecules can be employed. Possible binding partners will be described in the following by way of example. It should be noted, however, that a plurality of other possible targets can be added to this list. The term "is not a natural binding target" as used herein refers to a target with affinity of at least 10 fold higher to the binding protein of the invention than for di-ubiquitin. "not a natural binding target" further implies that the binding activity of the binding molecules of the invention is created de novo. In other words, a "natural binding target" would bind to unmodified ubiquitin (for example, SEQ ID NO: 1 or at least 95% identical sequences such as SEQ ID NO: 2) or unmodified di-ubiquitin (for example, SEQ ID NO: 4 or at least 95% identical sequences such as SEQ ID NO: 43) with at least 10 fold lower affinity than the binding proteins of the invention. The term "dissociation constant" or "$K_D$" defines the specific binding affinity. A high affinity corresponds to a low value of $K_D$. Thus, the expression "a $K_D$ of at least e.g. $10^{-7}$ M" means a value of $10^{-7}$M or lower (binding more tightly). $1 \times 10^{-7}$M corresponds to 100 nM. A value of $10^{-5}$ M and below down to $10^{-12}$ M can be considered as a quantifiable binding affinity. Depending on the application a value of $10^{-7}$ to $10^{-12}$ M is preferred for e.g. chromatographic applications or for e.g. diagnostic or therapeutic applications. In accordance with the invention the affinity for the target binding should be in the range of less than $1 \times 10^{-6}$M (1000 nM). Final target binding affinity should be ideally below $10^{-9}$M (1 nM).

The term "ubiquitin" or "unmodified ubiquitin" refers to ubiquitin in accordance with SEQ ID NO: 1 (wild type ubiquitin), according to SEQ ID NO: 2 (point mutations in positions F45W, G75A, G76A which do not influence binding to a target), according to SEQ ID NO: 4 (point mutations for example in positions G75A, G76A, F121W, G151A, G152A; also referred to as "di-ubiquitin" herein; corresponds to clone 139090) according to SEQ ID NO: 43 (two wild type ubiquitin moieties directly fused together without additional peptide linker; also referred to as "di-ubiquitin" herein) or which do not influence binding to a target) and according to the following definition.

Particularly preferred are ubiquitins from mammals, e.g. humans, primates, pigs, and rodents. On the other hand, the ubiquitin origin is not relevant since according to the art all eukaryotic ubiquitins are highly conserved and the mammalian ubiquitins examined up to now are even identical with respect to their amino acid sequence. In addition, ubiquitin from any other eukaryotic source can be used. For instance ubiquitin of yeast differs only in three amino acids from the wild-type human ubiquitin (SEQ ID NO: 1).

The term "di-ubiquitin" refers to a linear protein wherein two ubiquitin moieties are directly fused to each other in head to tail orientation. The term "di-ubiquitin" refers to according to SEQ ID NO: 4 (point mutations in positions G75A, G76A, F121W, G151A, G152A; corresponds to clone 139090; two ubiquitin moieties directly fused together) or to proteins with at least 95% amino acids identity to SEQ ID NO: 4, for example, according to SEQ ID NO: 43 (two wild type ubiquitin moieties directly fused together). A "di-ubiquitin mutein" according to this invention refers to a di-ubiquitin of SEQ ID NO: 43 or SEQ ID NO: 4 having modifications in at least 12, 13, or 14 amino acid positions, preferably in positions R42, I44, H68, V70, R72, L73, R74, K82, L84, Q138, K139, E140, S141, and T142, and is capable of binding to selected targets.

The terms "Affilin" and "ubiquitin mutein" and "modified ubiquitin" are all used synonymously and can be exchanged. The term "ubiquitin mutein" and "Affilin" and "modified ubiquitin" as used herein refers to derivatives of ubiquitin which differ from said unmodified ubiquitin or di-ubiquitin by amino acid exchanges, insertions, deletions or any combination thereof, provided that the modified ubiquitin or ubiquitin mutein or di-ubiquitin mutein has a specific binding affinity to a target which is at least 10 fold lower or absent in unmodified ubiquitin or di-ubiquitin. This functional property of a di-ubiquitin mutein (Affilin) is a de novo created function.

The term "Affilin®" (registered trademark of Scil Proteins GmbH) refers to non-immunoglobulin derived binding proteins based on ubiquitin muteins. An Affilin is not a natural ubiquitin existing in or isolated from nature. The scope of the invention excludes unmodified ubiquitin. An Affilin molecule according to this invention comprises or essentially consists of two differently modified ubiquitin moieties linked together in a head-to-tail fusion (di-ubiquitin mutein). A "head-to-tail fusion" is to be understood as fusing two proteins together by connecting them in the direction (head) N—C—N—C— (tail) (tandem molecule), as described for example in EP2379581B1 which is incorporated herein by reference. The head part is designated as the first moiety and the tail part as the second moiety. In this head-to-tail fusion, the ubiquitin moieties may be connected directly without any linker, as shown in this invention. Alternatively, the fusion of ubiquitin moieties can be performed via linkers, for example, a polypeptide linker (e.g. for library SPVF, see Table 2).

The term "substitution" includes both conservative and non-conservative substitutions. "Conservative substitutions" may be made, for instance, on the basis of similarity in polarity, charge, size, solubility, hydrophobicity, hydrophilicity, and/or the amphipathic nature of the amino acid residues involved. Amino acids can be grouped into the following standard amino acid groups: (1) hydrophobic side chains: Ala (A), Met (M), Leu (L), Val (V), Ile (I), (2) acidic polar side chain: Asp (D), Glu (E), (3) basic side chain polarity: Lys (K), Arg (R), His (H), (4) aromatic amino acids: Trp (W), Tyr (Y), Phe (F), (5) polar amino acids: Thr (T), Ser (S), Asn (N), Gln (Q), (6) residues that influence chain orientation: Gly (G), Pro (P), and (7) Cys (C). As used herein, "conservative substitutions" are defined as exchanges of an amino acid by another amino acid listed within the same group of the standard amino acid groups shown above. For example, the exchange of Asp by Glu retains one negative charge in the so modified polypeptide. In addition, Gly and Pro may be substituted for one another based on their ability to disrupt α-helices. Some preferred conservative substitutions within the above groups are exchanges within the following sub-groups: (i) Ala, Val, Leu and Ile; (ii) Ser and Thr; (ii) Asn and Gln; (iv) Lys and Arg; and (v) Tyr and Phe. Given the known genetic code, and recombinant and synthetic DNA techniques, the skilled scientist can readily construct DNAs encoding the conservative amino acid variants. As used herein, "non-conservative substitutions" or "non-conservative amino acid exchanges" are defined as exchanges of an amino acid by another amino acid listed in a different group of the standard amino acid groups (1) to (7) shown above.

The term "fused" means that the components (for example, two ubiquitin moieties or two ubiquitin muteins) are linked by peptide bonds, either directly or via peptide linkers.

The term "fusion protein" relates to a protein comprising at least a first protein joined genetically to at least a second protein. A fusion protein is created through joining of two or more genes that originally coded for separate proteins. Thus, a fusion protein may comprise a multimer of different or identical binding proteins which are expressed as a single, linear polypeptide. Such fusion proteins may further comprise additional domains that are not involved in binding of the target, such as but not limited to, for example, multimerization moieties, polypeptide tags, polypeptide linkers.

The term "conjugate" as used herein relates to a protein comprising or essentially consisting of at least a first protein attached chemically to other substances such as to a second protein or a non-proteinaceous moiety. The conjugation can be performed by means of organic synthesis or by use of enzymes including natural processes of enzymatic post-translational modifications. Examples for protein conjugates are glycoproteins (conjugated protein with carbohydrate component) or lipoproteins (conjugated protein with lipid component). The molecule can be attached e.g. at one or several sites through any form of a linker. Chemical coupling can be performed by chemistry well known to someone skilled in the art, including substitution (e.g. N-succinimidyl chemistry), addition or cycloaddition (e.g. maleimide chemistry or click chemistry) or oxidation chemistry (e.g. disulfide formation). Some examples of non-proteinaceous polymer molecules which are chemically attached to protein of the invention are hydroxyethyl starch, polyethylene glycol, polypropylene glycol, dendritic polymers, or polyoxyalkylene and others.

A fusion protein or protein conjugate may further comprise one or more reactive groups or peptidic or non-peptidic moieties such as targets or therapeutically or diagnostically relevant molecules such as radionuclides or toxins. It may also comprise small organic or non-amino acid based compounds, e.g. a sugar, oligo- or polysaccharide, fatty acid, etc. Methods for attaching a protein of interest to such non-proteinaceous components are well known in the art, and are thus not described in further detail here.

The term "amino acid sequence identity" refers to a quantitative comparison of the identity (or differences) of the amino acid sequences of two or more proteins. "Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity.

To determine the sequence identity, the sequence of a query protein is aligned to the sequence of a reference protein, for example, to SEQ ID NO: 4. Methods for alignment are well known in the art. For example, for determining the extent of an amino acid sequence identity of an arbitrary polypeptide relative to the amino acid sequence of SEQ ID NO: 4, the SIM Local similarity program is preferably employed (Xiaoquin Huang and Webb Miller (1991), Advances in Applied Mathematics, vol. 12: 337-357), that is freely available (see also: the ExPASy Bioinformatics Resource Portal website on the World Wide Web.). For multiple alignment analysis, ClustalW (Thompson et al. (1994) Nucleic Acids Res., 22(22): 4673-4680) or Clone Manager (Scientific & Educational Software) are preferably used.

In the context of the present invention, the extent of sequence identity between a modified sequence and the sequence from which it is derived (also termed: "parental sequence") is generally calculated with respect to the total length of the unmodified sequence, if not explicitly stated otherwise. Each amino acid of the query sequence that differs from the reference amino acid sequence at a given position is counted as one difference. An insertion or deletion in the query sequence is also counted as one difference. For example, an insertion of a linker between two ubiquitin moieties is counted as one difference compared to the reference sequence. The sum of differences is then related to the length of the reference sequence to yield a percentage of non-identity. The quantitative percentage of identity is calculated as 100 minus the percentage of non-identity. In this invention, in specific cases of determining the identity of the ubiquitin mutein aligned against di-ubiquitin (for example, SEQ ID NO: 4 or SEQ ID NO: 43), differences in positions 45, 75, 76, 121, 151, and/or 152 of di-ubiquitin are not counted, in particular, because they are not relevant for the novel binding capability of the ubiquitin mutein. The ubiquitin moiety can be modified in amino acid residues 45, 75, 76, 121, 151, and/or 152 of di-ubiquitin without affecting its binding capability; said modifications might, however, be relevant for achieving modifications in the biochemical properties of the ubiquitin mutein. Generally, the di-ubiquitin sequence used as starting material for the modifications has an amino acid identity of at least 95% amino acids, of at least 96%, or of at least 97% to SEQ ID NO: 4. Thus, a polypeptide which is, for example, 95% "identical" to a reference sequence may comprise, for example, five point mutations, e.g. substitutions, or four point mutations and one insertion, per 100 amino acids, compared to the reference sequence of SEQ ID NO: 4. An example is given in SEQ ID NO: 43.

Binding proteins of the invention comprise di-ubiquitin muteins wherein the two ubiquitin mutein moieties are linked directly without any linker to result in unique and high affinity binding proteins with substitutions at least in 12, 13, or 14 positions selected from R42, I44, H68, V70, R72, L73, R74, K82, L84, Q138, K139, E140, S141, and T142 of di-ubiquitin with between 85% and 92% sequence identity to di-ubiquitin. In addition, binding proteins of the invention can be genetically fused to other functional protein moieties. In the context of such fusion proteins of the invention the term "linker" refers to a single amino acid or a polypeptide that joins at least two other protein molecules covalently. The linker is genetically fused to the first and second protein or protein moieties to generate a single, linear polypeptide chain. The length and composition of a linker may vary between at least one and up to about 50 amino acids. Preferably, the linker length is between one and 30 amino acids. More preferably, the peptide linker has a length of between 1 and 20 amino acids; e.g. 1, 2, 3, 4, 5, 6, 7, 8, 9, 10, 11, 12, 13, 14, 15, 16, 17, 18, 19, or 20 amino acids.

It is preferred that the amino acid sequence of the peptide linker is not immunogenic to human beings, stable against proteases and optionally does not form a secondary structure. An example is a linker comprised of small amino acids such as glycine, serine or alanine. The linkers can be glycine-rich (e.g., more than 50% of the 25 residues in the linker can be glycine residues). Preferred are glycine-serine-linker of variable length consisting of glycine and serine residues only. In general, linkers of the structure (SGGG; SEQ ID NO: 44)$_n$ or permutations of SGGG (SEQ ID NO: 44), e.g. (GGGS; SEQ ID NO: 45)$_n$, can be used wherein n can be any number between 1 and 6, preferably 1 or 2 or 3. Also preferred are linkers comprising further amino acids. Other linkers for the genetic fusion of proteins are known in the art and can be used.

In case of chemical conjugates of the binding proteins of the invention, the term "linker" refers to any chemical moiety which connects the binding protein with other proteinaceous or non-proteinaceous moieties either covalently or non-covalently, e.g., through hydrogen bonds, ionic or van der Waals interactions, such as two complementary nucleic acid molecules attached to two different moieties that hybridize to each other, or chemical polymers such as polyethylene glycol or others. Such linkers may comprise reactive groups which enable chemical attachment to the protein through amino acid side chains. Such linkers and reactive groups are well-known to those skilled in the art and not described further.

Advantages of the Invention

Compared to conventional monoclonal antibodies, a significant advantage of the binding proteins of the invention is the reduced complexity in terms of (i) reduced size (e.g. of maximal about 152 amino acids), (ii) simple molecular structure (e.g., one chain compared to four chains of an antibody), and (iii) no posttranslational modifications required for full functionality. These factors contribute to an easy handling of the molecules including simple genetic engineering as well as easy production and purification methods.

Although binding molecules based on antibody formats are well-known, there are still major drawbacks, for example suboptimal physicochemical properties or low production yields of those molecules. The binding proteins of the invention provide simple molecular formats which are easy to engineer and the resulting molecules have favorable physicochemical properties (such as solubility and stability), high-level expression and allow easy production methods.

Methods for the generation of ubiquitin muteins having modifications selected from positions 2, 4, 6, 62, 63, 64, 65, 66 of one ubiquitin moiety (SEQ ID NO: 1) were described (see EP1626985B1). Another method for identifying heteromultimeric modified ubiquitin molecules relates to heteromultimeric modified ubiquitin molecules with substitutions selected from positions 2, 4, 6, 8, 62, 63, 64, 65, 66, 68 of two ubiquitin moieties fused with a peptide linker (see EP2379581B1).

Although these ubiquitin mutein proteins represent high affinity binding proteins and efficient methods for their production and identification, there are disadvantages such as the low solubility of the libraries required for the identification of such binding molecules. The libraries known in the art are prone to low solubility and low expression rates, resulting in inefficient screening procedures and adding complexity to the process, lowering yields, and increasing costs.

Taken together, due to several limitations of known binding proteins and their methods of generation and identification there was a strong need in the prior art to provide novel binding proteins with improved properties. In this context, there was a need for novel generation and identification methods, in particular for highly soluble and expressable libraries encoding binding proteins based on di-ubiquitin muteins.

An advantage of the invention is the method of generation and identification of novel binding proteins by providing libraries with enhanced solubility and expression rates. An advantage of the novel binding proteins of the invention is that they bind with high efficiency to targets.

The present invention provides libraries with a combination of defined positions for randomization for identifying artificial binding proteins based on di-ubiquitin muteins that are particularly well-suited for binding targets but overcome the disadvantages of the prior art.

DESCRIPTION OF PREFERRED EMBODIMENTS OF THE INVENTION

One aspect of the invention relates to a binding protein of the invention having binding affinity ($K_D$) of less than 1000 nM to a target wherein the affinity of the binding protein to the target is at least 10 fold higher than for SEQ ID NO: 4. The binding protein comprises or essentially consists of or consists of an amino acid sequence wherein at least 12 amino acids selected from positions R42, I44, H68, V70, R72, L73, R74, K82, L84, Q138, K139, E140, S141, and T142 of di-ubiquitin are substituted wherein the binding protein has at least 85% sequence identity to di-ubiquitin. Thus, the binding proteins show maximal 92% sequence identity to di-ubiquitin. It is unexpected and surprising that the specific combination of at least said 12 amino acids in said positions is generating a high affinity binding protein for a target wherein said target affinity is at least 10 fold higher than for SEQ ID NO: 4.

The preferred binding proteins comprise 152 amino acids with at least 85%, preferably at least 87% identity to di-ubiquitin (SEQ ID NO: 4), provided that at least 12 positions selected from R42, I44, H68, V70, R72, L73, R74, K82, L84, Q138, K139, E140, S141, and T142 are substituted. Surprisingly, the specific combination of substitutions in said 12, 13, or 14 positions of di-ubiquitin (SEQ ID NO: 4) result in high affinity binding proteins. These proteins are artificial proteins that are created de novo. The binding proteins of the invention do not exist in nature. Examples for de novo created binding proteins are provided in SEQ ID NOs: 5-42.

It is preferred that a binding protein of the invention has additionally 0, 1, 2, 3, 4, 5, or 6 substitutions. In other words, it is preferred that a binding proteins of the invention has at least 85%, 86%, 87%, 88%, 89%, 90%, 91%, preferably at least 85% or 87% sequence identity to maximal 92% sequence identity to di-ubiquitin (SEQ ID NO: 4). The binding protein of the invention is substituted in positions R42, I44, H68, V70, R72, L73, R74, K82, L84, Q138, K139, E140, S141, and T142 of di-ubiquitin and has no further substitution (for example, SEQ ID NOs: 29, 33, 39, 40, 41, 42), one additional substitution (for example, SEQ ID NOs: 27, 28, 31, 32), two additional substitutions (for example, SEQ ID NOs: 14, 16, 21, 25, 26, 30, 35), three additional substitutions (for example, SEQ ID NOs: 6, 12, 13, 15, 17, 18, 20, 34, 36), four additional substitutions (for example, SEQ ID NOs: 10, 11, 19, 22, 23, 24), five additional substitutions (for example, SEQ ID NOs: 5, 7, 8, 9), or six additional substitutions (for example, SEQ ID NO: 37). For example, further 1, 2, 3, 4, 5, or 6 substitutions in addition to substitutions in positions R42, I44, H68, V70, R72, L73, R74, K82, L84, Q138, K139, E140, S141, and T142 of di-ubiquitin may be preferably selected from positions 6, 10, 11, 15, 20, 21, 23, 28, 31, 34, 36, 40, 46, 48, 49, 52, 58, 62, 63, 75, 78, 88, 92, 95, 96, 98, 114, 120, 124, 131, 133, I44, 147 of di-ubiquitin, more preferably selected from positions 46, 78, 92, 23, 52.

A binding protein of the invention is having a specific binding affinity ($K_D$) of at least 1000 nM, preferably at least 100 nM, preferably at least 10 nM, when determined by surface plasmon resonance, to a target wherein said target is not a natural binding target of di-ubiquitin (i.e. affinity of the binding protein to the target is at least 10 fold higher than for di-ubiquitin. For example, a binding protein of the invention is having a specific binding affinity of at least 700 nM, preferably at least 100 nM, preferably at least 10 nM, to peptide targets as for example Her2, CD3, EGFR, or EpCAM, when determined by surface plasmon resonance.

The present invention has been successfully established on the following representative protein targets: Her2, CD3, EpCAM, and EGFR. It is to be understood that these protein targets have only been selected to show that the presently described methods can be successfully carried out by a person skilled in the art without undue burden after having received the information provided herein. The invention is not restricted to these specific protein targets but can be performed on all or most of target molecules known in the art. Those targets can be selected by the skilled artisan within his general knowledge of the art.

Her2 (Human Epidermal Growth Factor Receptor 2; synonym names are ErbB-2, Neu, CD340 or p185) is a 185-kDa receptor first described in 1984 (Schlechter et al (1984) Nature 312:513-516). Amplification or overexpression of this gene has been shown to play an important role in the pathogenesis and progression of certain aggressive types of breast cancer, and Her2 is known as an important biomarker and target of therapy for the disease. Other tumors where Her2 plays a role include ovarian cancer and gastric cancer.

The epidermal growth factor receptor (EGFR; synonym names are HER1 or ErbB1) is the cell-surface receptor for members of the epidermal growth factor family (EGF-family). EGFR is known for its role in lung cancer, head and neck cancer and colorectal cancer. The involvement in many cancers validates EGFR as a useful therapeutic target and supports the search for improved understanding of receptor biology and the development of improved therapies. Potential causes of the modest efficacy of current EGFR antagonists include the inability to effectively compete with target, especially in the presence of autocrine signaling; insufficient down-regulation of receptor; lack of inhibition of constitutively active EGFRvIII; and mutational escape. Thus, novel binders capable of downregulation and/or inhibition via different modes of action would be beneficial and multivalent and/or multispecific binders against EGFR hold the potential to be more effective in this respect.

epCAM (epithelial cell adhesion molecule) is a 30 to 40 kDa transmembrane glycoprotein involved in cell signaling, migration, proliferation, and differentiation. The protein is expressed in neoplasms derived from epithelia and is thus a marker for the diagnosis of various cancers.

CD3 (cluster of differentiation 3) is a cell-surface co-receptor on T-cells. The protein complex CD3 is composed of four distinct chains that associate with a T-cell receptor (TCR) to generate an activation signal in T lymphocytes.

Drugs binding to CD3 might be useful in immunosuppressant therapies for example for autoimmune diseases such as diabetes type 1.

The term "Her2" or "EGFR" or "EpCAM" or "CD3" comprises all polypeptides which show a sequence identity of at least 70%, 80%, 85%, 90%, 95%, 96% or 97% or more, or 100% to accession number NP_004439 (Her2), to accession number NP_005219 (EGFR), to accession number NP_002354.2 (EpCAM), or to accession number P077661, respectively, and have the functionality of Her2, EGFR, EpCAM, or CD3, respectively. The extracellular domain of Her2 is represented by uniprot accession number P04626 (residues 1-652). The extracellular domain of human EGFR is represented by uniprot accession number P00522 (residues 1-645). The extracellular domain of human EpCAM is represented by uniprot accession number P16422 (residues 1-265).

Many selected examples of binding proteins with at least 12 substitutions in positions 42, 44, 68, 70, 72, 73, 74, 82, 84, 138, 139, 140, 141, and 142 of di-ubiquitin are provided in this invention. The binding proteins of the invention bind to the non-natural targets of di-ubiquitin with measurable binding affinity of less than 1000 nM, less than 500 nM, less than 100 nM, less than 20 nM, less than 10 nM (for example, SEQ ID NOs: 6, 14, 15, 18, 22, 24, 25, 26, 28, 35, 36, 38), and more preferred less than 1 nM (for example, SEQ ID NOs: 7, 8, 9, 10, 11, 12, 13, 16, 17, 19, 20, 23). The unmodified di-ubiquitin (SEQ ID NO: 4) does not naturally bind to protein targets for example Her2, epCAM, CD3, or EGFR with any measurable binding affinity. All binding proteins of the invention show de novo created binding to targets with high affinity, i.e. wherein the affinity of the binding protein to the target is at least 10 fold higher than for di-ubiquitin. Specific examples for binding proteins are provided in FIG. 3, Table 1, and Table 4. Examples for Her2 binding proteins are given in SEQ ID NOs: 5-38, for CD3 binding proteins in SEQ ID NO: 39, for EpCAM binding proteins in SEQ ID NO: 40 and 41, and for EGFR binding proteins in SEQ ID NO: 42.

Another preferred binding protein (Affilin-141975) is substituted in 20 amino acids of di-ubiquitin (substitutions in amino acids in positions 42, 44, 68, 70, 72, 73, 74, 82, 84, 138, 139, 140, 141, 142 and in positions 52, 75, 78, 96, 114, 131). The Her2 binding protein Affilin-141884 shows 87% identity to di-ubiquitin (SEQ ID NO: 4). The Her2 binding capability was confirmed by FACS analysis (SK-Br-3 cells).

For example, a preferred binding protein (Affilin-142628) is substituted in 18 amino acids of di-ubiquitin (substitutions in amino acids in positions 42, 44, 68, 70, 72, 73, 74, 82, 84, 138, 139, 140, 141, 142 and in positions 23, 78, 92, 46). The Her2 binding protein Affilin-142628 shows 88% identity to di-ubiquitin (SEQ ID NO: 4). The Her2 binding protein shows strong binding to tumor tissues expressing the target.

Another preferred binding protein (Affilin-141884) is substituted in 16 amino acids of SEQ ID NO: 24 (substitutions in amino acids in positions 42, 44, 68, 70, 72, 73, 74, 82, 84, 138, 139, 140, 141, 142 and in positions 27 and 78). The Her2 binding protein Affilin-141884 shows 90.5% identity to di-ubiquitin (SEQ ID NO: 4). The Her2 binding protein shows strong binding to tumor tissues expressing the target.

Another preferred binding protein (Affilin-141926) is substituted in 15 amino acids of di-ubiquitin (substitutions in amino acids in positions 42, 44, 68, 70, 72, 73, 74, 82, 84, 138, 139, 140, 141, 142 and in position 78). The Her2 binding protein Affilin-141884 shows 90% identity to di-ubiquitin (SEQ ID NO: 4).

Other preferred binding proteins (for example, Affilin-144160, Affilin 143488, Affilin-143283, Affilin-142265) are substituted in 14 amino acids of di-ubiquitin (substitutions in amino acids corresponding to positions 42, 44, 68, 70, 72, 73, 74, 82, 84, 138, 139, 140, 141, 142). The binding proteins shows 91% identity to di-ubiquitin (SEQ ID NO: 4).

Preferred substitutions of the Her2 binding protein based on di-ubiquitin are substitutions of amino acids selected from position 70 and 140 by aromatic amino acids. Further preferred substitutions of the Her2 binding protein based on di-ubiquitin are substitutions of amino acids selected from position 42 by a polar amino acid, position 44 is substituted by a hydrophobic or polar amino acid, position 68 is substituted by an aromatic amino acid, position 72 is substituted by a polar or aromatic amino acid, position 73 is substituted by any amino acid but not basic or acidic amino acid, position 74 is substituted by an aromatic, basic or polar amino acid, position 82 is substituted by any amino acid but not basic or acidic amino acid, position 84 is substituted by a basic or acidic amino acid, position 138 is substituted by a basic or acidic or polar amino acid, position 139 is substituted by acidic or hydrophobic amino acid or Glycine, position 141 is substituted by hydrophobic or polar or basic amino acid, and/or position 142 is substituted b a hydrophobic or polar amino acid. Preferred substitutions of the Her2 binding protein based on di-ubiquitin are selected from R42T, R42S, R42L, I44A, I44V, I44S, I44T, H68W, H68Y, H68F, V70Y, V70W, R72T, R72F, R72G, R72Y, L73W, L73S, L73V, L73I, R74Y, R74S, R74N, R74K, K82T, K82L, K82N, K82I, K82Y, L84H, L84D, L84E, L84S, Q138S, Q138R, Q138E, K139E, K139G, K139L, E140W, S141A, S141R, T142I, T142L, and/or T142N. Further preferred are Her2 binding proteins with a specific combination of amino acid substitutions in SEQ ID NO: 4, for example, at least R42T, I44A, H68W, V70Y, R72T, L73W, R74Y, K82T, L84H (for example, SEQ ID NOs: 7-29). Other preferred Her2 binding proteins with a specific combination of amino acid substitutions in di-ubiquitin, are for example at least R42S, I44V, H68Y, V70Y, R72F, L73S, K82L, L84D (for example, SEQ ID NOs: 34, 35, 36, and 36). Further preferred are Her2 binding proteins with a specific combination of amino acid substitutions in di-ubiquitin, for example, Q138S, K139E, E140W, S141A, T142I (for example, in SEQ ID NOs: 5, 7-29, 33, 36, 37), or Q138R, K139G, E140W, T142L (for example, in SEQ ID NOs: 6, 34, 35), or Q138 E, K139L, E140W, S141R, T142N (for example, in SEQ ID NOs: 30, 31, 32).

Table 1 lists examples for substitutions of di-ubiquitin in order to generate a novel binding protein (in addition to FIG. 1). All binding proteins (for example, SEQ ID NOs: 39-42) are substituted in 14 positions selected from positions 42, 44, 68, 70, 72, 73, 74, 82, 84, 138, 139, 140, 141, and 142 of di-ubiquitin. SEQ ID NO: 39 binds to the protein target CD3, SEQ ID NOs: 40-41 bind to the protein target epCAM, and SEQ ID NO: 42 binds to the protein target EGFR.

TABLE 1

| SEQ | Affilin | target | 42 | 44 | 68 | 70 | 72 | 73 | 74 | 82 | 84 | 138 | 139 | 140 | 141 | 142 |
|---|---|---|---|---|---|---|---|---|---|---|---|---|---|---|---|---|
| 42 | 142265 | EGFR | E | T | W | E | Y | A | K | Q | I | T | R | L | V | W |
| 41 | 143283 | epCAM | R | Q | G | L | T | Q | R | Y | N | F | R | F | Q | H |
| 40 | 143488 | epCAM | Y | Y | K | Y | W | R | V | A | G | G | S | Y | G | Y |
| 39 | 144160 | CD3 | W | W | K | W | V | D | K | Y | R | A | L | E | S | G |

It is preferred that the binding proteins of the invention comprise amino acid sequences that exhibits at least 85% or at least 87% or at least 91% or at least 94% or at least 96% sequence identity to one or more of the amino acid sequences of SEQ ID NO: 5-42.

The further characterization of binding proteins can be performed in the form of soluble proteins. The appropriate methods are known to those skilled in the art or described in the literature. The methods for determining the binding affinities are known per se and can be selected for instance from the following methods known in the art: Surface Plasmon Resonance (SPR) based technology, Bio-layer interferometry (BLI), enzyme-linked immunosorbent assay (ELISA), flow cytometry, fluorescence spectroscopy techniques, isothermal titration calorimetry (ITC), analytical ultracentrifugation, radioimmunoassay (RIA or IRMA) and enhanced chemiluminescence (ECL). Some of the methods are described in the Examples below.

For stability analysis, for example spectroscopic or fluorescence-based methods in connection with chemical or physical unfolding are known to those skilled in the art. Exemplary methods for characterization of Her2 binding proteins are outlined in the Examples section of this invention.

A biochemical binding analysis of binding proteins of the invention to given targets is summarized in Table 4 and further described in the Examples. In an embodiment of this aspect, the Her2-binding protein has a dissociation constant $K_D$ to human Her2 in the range between 0.01 nM and 700 nM, more preferably between 0.05 nM and 500 nM, more preferably between 0.1 nM and 100 nM, more preferably between 0.1 nM and 20 nM, more preferably between 0.1 nM and 10 nM. The dissociation constant $K_D$ can be determined for example by ELISA or by surface plasmon resonance assays. Typically, the dissociation constant $K_D$ is determined at 20° C., 25° C. or 30° C. If not specifically indicated otherwise, the $K_D$ values recited herein are preferably determined at 25° C. by surface plasmon resonance.

Another aspect of the invention covers a binding protein of the invention and further at least one additional protein or molecule. The additional protein can be a second binding protein with identical or different specificity for an antigen as the first binding protein. One embodiment of the invention covers a fusion protein or a conjugate comprising an Affilin-antibody fusion protein or conjugate, optionally further fused with or conjugated to a moiety preferably selected from at least one member of the groups (i), (ii) and (iii) consisting of (i) a moiety modulating pharmacokinetics selected from a PEG, a HSA, an albumin-binding peptide, or an immunoglobulin or immunoglobulin fragments, a polysaccharide, and, (ii) a therapeutically active component, optionally selected from a monoclonal antibody or a fragment thereof, a cytokine, a chemokine, a cytotoxic compound, an enzyme, or derivatives thereof, or a radionuclide, and (iii) a diagnostic component, optionally selected from a fluorescent compound, a photosensitizer, a tag, an enzyme or a radionuclide. The conjugate molecule can be attached e.g. at one or several sites through a peptide linker sequence or a carrier molecule.

Further conjugation with proteinaceous or non-proteinaceous moieties to generate protein conjugates according to the invention can be performed applying chemical methods well-known in the art. In particular, coupling chemistry specific for derivatization of cysteine or lysine residues is applicable. In case of the introduction of non-natural amino acids further routes of chemical synthesis are possible, e.g. "click chemistry" or aldehyde specific chemistry and others.

Conjugates thus obtained can be selected from one or more of the following examples: (i) conjugation of the protein via lysine residues; (ii) conjugation of the protein via cysteine residues via maleimide chemistry; in particular, cysteine residues can be specifically introduced and can be located at any position suitable for conjugation of further moieties, (iii) peptidic or proteinogenic conjugations. These and other methods for covalently and non-covalently attaching a protein of interest to other functional components are well known in the art, and are thus not described in further detail here.

A further embodiment relates to binding proteins according to the invention, further comprising a moiety modulating pharmacokinetics or biodistribution, preferably selected from PEG, HSA, or an immunoglobulin or immunoglobulin fragments, for example an Fc fragment. Several techniques for producing proteins with extended half-life are known in the art.

In a further aspect of the invention, a binding protein of the invention or fusion protein or conjugate is used in medicine, in particular in a method of medical treatment or diagnosis, preferably in cancer or autoimmune disorders.

For example, the membrane proteins Her2, EGFR, and epCAM are known to be upregulated in tumor cells, resulting in uncontrolled growth of tumor cells and in the formation of metastases. New therapies for cancer patients include an inhibition of EGFR by targeted therapeutics such as for example the monoclonal antibodies Cetuximab (Erbitux®) or Panitumumab (Vectibix®) or an inhibition of Her2 by for example Trastuzumab (Herceptin®) or Pertuzumab (Perjeta®). T-DM1, an antibody-drug conjugate, is highly effective against breast, uterine and ovarian carcinosarcomas overexpressing Her2. For EGFR, further monoclonal antibodies are in development, for example, Zalutumumab (HuMax-EGFr) and Nimotuzumab (h-R3 or Theraloc). For EpCAM, monoclonal antibodies such as Edrecelolomab are Catumaxomab in development.

Overexpression of Her2 and EGFR was described in a wide variety of cancers. For example, overexpression of Her2 occurs in approximately 15-30% of breast cancers and 10-30% of gastric/gastroesophageal cancers, and has also been observed in other cancers like ovary, endometrium, bladder, lung colon, head and neck. Thus, the pharmaceutical composition comprising the binding protein of the invention, can be used for treatment of cancer in which the target is relevant for the development of the disease including but not limited to particularly breast, ovarian, gastric, but also in lung, head and neck, cervical, prostate, pancreas, and others.

EpCAM plays different roles and is heterogeneous overexpressed in carcinomas, but also in cancer stem cells. EpCAM is found not only in tumors but also in normal epithelium. Further EpCAM plays a role in a genetic disorder (Lynch syndrome) leading to an increased cancer risk.

CD3 is expressed in stem cells from and is required for T-cell activation. Antibodies such as Otelixizumab (TRX4) are in development for immunosuppressant therapies for autoimmune diseases (e.g. diabetes type 1).

The compositions contain a therapeutically or diagnostically effective dose of the binding protein of the invention. The amount of protein to be administered depends on the organism to be treated, the type of disease, the age and weight of the patient and further factors known per se.

The invention covers a pharmaceutical composition comprising the binding protein, fusion protein or conjugate or the nucleic acid molecule of the invention, the vector of the invention, and/or the host cell or virus and a pharmaceutically acceptable carrier. The invention further covers a diagnostic agent comprising the binding protein or conjugate or the nucleic acid molecule of the invention, the vector of the invention, and/or the host cell or non-human host with a diagnostically acceptable carrier. The compositions contain a pharmaceutically or diagnostically acceptable carrier and optionally can contain further auxiliary agents and excipients known per se. These include for example but are not limited to stabilizing agents, surface-active agents, salts, buffers, coloring agents etc.

The pharmaceutical composition comprising the binding protein can be in the form of a liquid preparation, a lyophilisate, a cream, a lotion for topical application, an aerosol, in the form of powders, granules, in the form of an emulsion or a liposomal preparation. The compositions are preferably sterile, non-pyrogenic and isotonic and contain the pharmaceutically conventional and acceptable additives known per se. In addition, reference is made to the regulations of the U.S. Pharmacopoeia or Remington's Pharmaceutical Sciences, Mac Publishing Company (1990).

In the field of human and veterinary medical therapy and prophylaxis pharmaceutically effective medicaments containing at least one binding protein in accordance with the invention can be prepared by methods known per se. Depending on the galenic preparation these compositions can be administered parentally by injection or infusion, systemically, intraperitoneally, intramuscularly, subcutaneously, transdermally or by other conventionally employed methods of application. The type of pharmaceutical preparation depends on the type of disease to be treated, the route of administration, the severity of the disease, the patient to be treated and other factors known to those skilled in the art of medicine.

In a still further aspect the invention discloses diagnostic compositions comprising binding protein according to the invention specifically binding specific targets or its isoforms together with diagnostically acceptable carriers. Since enhanced Her2, EGFR, and epCAM expression is correlated with tumor malignancy, it is desirable to develop diagnostics for non-invasive imaging in order to gain information about the Her2, EGFR, and epCAM expression in patients. Furthermore, Her2, EGFR, and epCAM imaging could be useful for the assessment of the response of a patient to a therapeutic treatment. For example, using a protein of the invention labelled with a suitable radioisotope or fluorophore can be used for non-invasive imaging to determine the location of tumors and metastasis (for review see for example Milenic et al. 2008 Cancer Biotherapy & Radiopharmaceuticals 23: 619-631; Hoeben et al. 2011, Int. Journal Cancer 129: 870-878). Due to their pharmacokinetic characteristics, intact antibodies are not suitable for routine imaging. Due to their small size and high affinity, labelled fusion proteins of the invention are expected to be much better suited for use as diagnostics for imaging.

It is expected that a protein of the invention can be advantageously applied in therapy. In particular, the molecules are expected to show superior tumor targeting effect and desired biodistribution and thus, reduced side effects. Pharmaceutical compositions of the invention may be manufactured in any conventional manner.

In one embodiment of the invention, novel binding proteins given targets, preferably protein or peptide targets, are provided wherein the binding proteins comprise substitutions in 12, 13, or 14 positions corresponding to positions 42, 44, 68, 70, 72, 73, 74, 82, 84, 138, 139, 140, 141, and 142 of di-ubiquitin. Further key aspects of the invention cover the production of the binding proteins and the selection of the muteins of di-ubiquitin.

Binding molecules of the invention may be prepared by any of the many conventional and well known techniques such as plain organic synthetic strategies, solid phase-assisted synthesis techniques or by commercially available automated synthesizers. On the other hand, they may also be prepared by conventional recombinant techniques alone or in combination with conventional synthetic techniques. Conjugates according to the present invention may be obtained by combining compounds by chemical methods, e.g. lysine or cysteine-based chemistry, as described herein above.

According to another aspect of the invention, an isolated polynucleotide encoding a binding protein of the invention is provided.

In a further embodiment the invention relates to a vector comprising the nucleic acid molecule of the invention. A vector means any molecule or entity (e.g., nucleic acid, plasmid, bacteriophage or virus) that can be used to transfer protein coding information into a host cell.

The present invention furthermore relates to an isolated cell comprising the nucleic acid molecule of the invention or the vector of the invention. Suitable host cells include prokaryotes or eukaryotes. Various mammalian or insect cell culture systems can also be employed to express recombinant proteins. The invention also relates to a host cell carrying the vector of the invention. A host cell is a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

In another aspect is provided a method of producing the binding protein of the invention, comprising the steps of a) culturing the host cell of the invention under conditions suitable for the expression of the binding protein and b) isolating the produced binding protein.

One embodiment of the present invention is directed to a method for the preparation of a binding protein according to the invention as detailed above, said method comprising the following steps: (a) preparing a nucleic acid encoding a binding protein as defined above, (b) introducing said nucleic acid into an expression vector; (c) introducing said expression vector into a host cell; (d) cultivating the host cell; (e) subjecting the host cell to culturing conditions under which a binding protein is expressed, thereby producing a binding protein as described above; (f) optionally isolating the binding protein produced in step (e).

Suitable conditions for culturing a prokaryotic or eukaryotic host are well known to the person skilled in the art. Cultivation of cells and protein expression for the purpose of protein production can be performed at any scale, starting from small volume shaker flasks to large fermenters, applying technologies well-known to any skilled in the art.

Following the expression of the di-ubiquitin mutein according to the invention, the binding protein is optionally isolated. Methods of isolation of the polypeptide produced are well-known in the art and comprise without limitation method steps such as ion exchange chromatography, gel filtration chromatography (size exclusion chromatography), or affinity chromatography. Further purification of binding proteins comprises methods known to someone skilled in the art. The selected methods depend on several factors known per se to those skilled in the art, for example the expression vector used, the host organism, the intended field of use, the size of the protein and other factors. For simplified purification the protein modified according to the invention can be fused to other peptide sequences having an increased affinity to separation materials. Preferably, such fusions are selected that do not have a detrimental effect on the functionality of the di-ubiquitin muteins or can be separated after the purification due to the introduction of specific protease cleavage sites. Such methods are also known to those skilled in the art.

Isolation of purified protein can be performed applying conventional methods and technologies well known in the art, such as centrifugation, precipitation, flocculation, different embodiments of chromatography, filtration, dialysis, concentration and combinations thereof, and others.

A further aspect of the invention relates to a method for the generation of a binding protein of the invention which binds to a given target with a dissociation constant ($K_D$) of 1000 nM or lower, said method comprising (a) subjecting nucleotide triplets of a nucleic acid molecule of di-ubiquitin to mutagenesis in 12, 13, or 14 positions coding for amino acid positions corresponding to positions R42, I44, H68, V70, R72, L73, R74, K82, L84, Q138, K139, E140, S141, and T142 of the linear polypeptide sequence of di-ubiquitin (SEQ ID NO: 4), (b) resulting in one or more di-ubiquitin mutein nucleic acid molecule(s), (c) expressing the one or more di-ubiquitin mutein nucleic acid molecule(s) obtained in (b) in a suitable expression system, (d) enriching the one or more di-ubiquitin mutein(s) having a dissociation constant ($K_D$) of 1000 nM or lower for the given target by means of selection and/or isolation, (e) wherein the affinity to the target is at least 10 fold higher than for di-ubiquitin. Different procedures known per se are available for mutagenesis, such as methods for site-specific mutagenesis, methods for random mutagenesis, mutagenesis using PCR or similar methods. All methods are known to those skilled in the art.

In one preferred embodiment of the invention, two ubiquitin moieties are directly linked in head to tail orientation to result a protein of 152 amino acids. Each mutein is based on a common scaffold represented by the amino acid sequence MQIFVKTLTGKTITLEVEPSDTIENVKAK-IQDKEGIPPDQQXLXFAGKQLEDGRTLSDY-NIQKESTLXLXLXXXAAMQ IFVXTXTGKTITLEVE-PSDTIENVKAKIQDKEGIPPDQQRLIWAGKQLEDGR-TLSDYNIXXXXXLHLVLRLRAA (SEQ ID NO: 3), wherein X individually corresponds to an amino acid residue selected from S, Y, W, V, H, R, D, N, E, Q, G, K, F, T, A, L, I, or F (not allowed are M, C, and P).

As a state-of-the-art method for library synthesis the favorable triplet technology (Morphosys Slonomics) is capable of synthesizing random libraries with an even (or uneven, if wanted) distribution of e.g. the 20 natural amino acids. Assuming a random distribution of the 20 natural amino acids at e.g. 14 positions generates a pool of 20 to the power of 14 ($20^{14}$) theoretical di-ubiquitin muteins, each with a different amino acid composition and potentially different binding properties. Preferably, insertion of amino acid cysteine is avoided at all randomized positions resulting in $19^{14}$ theoretical di-ubiquitin muteins. This large pool of genes constitutes a library of different Affilin molecules.

A "randomly modified nucleotide or amino acid sequence" is a nucleotide or amino acid sequence which in a number of positions has been subjected to substitution, insertion, or deletion by nucleotides or amino acids, the nature of which cannot be predicted. In many cases the random nucleotides (amino acids) or nucleotide (amino acid) sequences inserted will be "completely random" (e. g. as a consequence of randomized synthesis or PCR-mediated mutagenesis). However, the random sequences can also include sequences which have a common functional feature (e. g. reactivity with a target of the expression product) or the random sequences can be random in the sense that the ultimate expression product is of completely random sequence with e. g. an even distribution of the different amino acids.

The mutagenized nucleic acid molecule comprising randomized nucleotide triplets coding 12, 13, or 14 positions selected from sequence positions R42, I44, H68, V70, R72, L73, R74, K82, L84, Q138, K139, E140, S141, and T142 is resulting in one or more mutein nucleic acid molecule(s) which will be expressing the one or more mutein nucleic acid molecule(s) obtained in (b) in a suitable expression system.

In some embodiments, the application provides libraries comprising a plurality of the non-naturally occurring binding polypeptides based on di-ubiquitin muteins as described herein. The libraries provided herein may comprise, for example, a sequence diversity of between at least about $10^{12}$, about $10^{13}$, or about $10^{14}$, or more polypeptides, each optional comprising a different amino acid sequence. In one embodiment of the invention, a nucleic acid library is provided encoding muteins of di-ubiquitin, wherein the amino acid residues selected from 12, 13, or 14 positions corresponding to amino acid positions 42, 44, 68, 70, 72, 73, 74, 82, 84, 138, 139, 140, 141, and 142 of SEQ ID NO: 3 (SEQ ID NO: 4) are substituted in the muteins by any amino acid except are M, C, or P. It is most preferred that the library comprises at least $19^{12}$ polypeptides each comprising a different amino acid sequence. Sequence differences between library members are responsible for the diversity present in the library. The library may take the form of a simple mixture (population; plurality) of polypeptides or nucleic acids. Advantageously, the nucleic acids are incorporated into expression vectors, in order to allow production of the polypeptides encoded by the nucleic acids.

The library can be cloned into a phagemid vector (e.g. pCD87SA (Paschke, M. and W. Hohne (2005). "Gene 350 (1): 79-88)). The library may be displayed on the surfaces of ribosomes, bacteriophage, viruses, bacteria, or yeast cells, preferably displayed on bacteriophage, and subjected to repeated rounds of panning against the respective target. Di-ubiquitin muteins from enriched phage pools are cloned into expression vectors for individual protein expression. Preferably, expression of the di-ubiquitin mutein enables screening for specific binding proteins by established techniques, such as ELISA on automated high-throughput screening platforms. Identified clones with desired binding properties are then sequenced to reveal the amino acid sequences of Affilin molecules. The identified binding protein may be subjected to further maturation steps, e.g. by generating additional libraries based on alterations of the identified sequences and repeated phage display, ribosomal display, panning and screening steps as described above.

The gene pool libraries obtained as described above can be combined with appropriate functional genetic elements which enable expression of proteins for selection methods such as display methods. A method for identifying a binding protein is provided with the affinity to the target of at least 10 fold higher than for di-ubiquitin comprising screening the library to identify a polypeptide that binds to the given target. A method for identifying a binding protein is thus comprising the following steps: a. providing a library wherein the amino acid residues selected from 12, 13, or 14 positions corresponding to 42, 44, 68, 70, 72, 73, 74, 82, 84, 138, 139, 140, 141, and 142 of SEQ ID NO: 3 (SEQ ID NO: 4) are randomized, b. providing a potential target to said library (for example, wherein the target is a protein or a peptide or a domain of a protein); c. contacting said library with said target; and d. identifying a binding protein by a screening process, wherein said binding protein binds to said target with a specific binding affinity of at least 1000 nM, and optionally isolating said binding protein with said binding affinity.

The expressed proteins are contacted according to the invention with a target molecule to enable binding of the partners to each other if a binding affinity exists. This process enables identification of those proteins which have a binding activity to the target molecule. See, for example, EP2379581B1, which is herewith incorporated by reference.

Contacting according to the invention is preferably performed by means of a suitable presentation and selection method such as the phage display, ribosomal display, mRNA display or cell surface display, yeast surface display or bacterial surface display methods, preferably by means of the phage display method. For complete disclosure, reference is made also to the following references: Hoess, Curr. Opin. Struct. Biol. 3 (1993), 572-579; Wells and Lowmann, Curr. Opin. Struct. Biol. 2 (1992), 597-604; Kay et al., Phage Display of Peptides and Proteins-A Laboratory Manual (1996), Academic Press. The methods mentioned above are known to those skilled in the art. In the phage display procedure described herein recombinant variations of ubiquitin are presented on a filamentous phage while the coding DNA of the presented variation is present at the same time packed in a single-stranded form in the phage envelope. Thus, in the frame of an affinity enrichment variations having certain properties can be selected from a library and their genetic information can be amplified by infection of suitable bacteria or added to another cycle of enrichment, respectively. Presentation of the di-ubiquitin mutein on the phage surface is achieved by genetic fusion to a signal sequence and a capsid or surface protein of the phage. Furthermore, the encoded protein can contain further functional elements such as an affinity tag or an antibody epitope for detection and/or purification by affinity chromatography or a protease recognition sequence for specific cleavage of the protein in the course of the affinity enrichment. Furthermore, an amber stop codon can be present between the gene for the di-ubiquitin mutein and the coding region of the phage capsid protein which is not recognized during translation in a suitable suppressor strain.

The bacterial vector suitable for the selection procedure in the context of the isolation of di-ubiquitin muteins and into which the gene cassette for the fusion protein described is inserted is referred to as phagemid. Among others, it contains the intergenic region of a filamentous phage (e.g. M13 or f1) or a portion thereof which in the case of a superinfection of the bacterial cell carrying the phagemid by means of helper phages results in the packaging of a covalently closed strand of phagemid DNA into a phage capsid.

Phage particles obtained can be selected with respect to the binding of the di-ubiquitin muteins presented thereon to any target by means of methods known to those skilled in the art. For this purpose, the presented di-ubiquitin muteins can be transiently immobilized to target substance and can be specifically eluted after non-binding variations have been separated. The phage particles obtained in this manner can be re-amplified and enriched by successive cycles of selection and amplification of di-ubiquitin muteins with binding properties to selected targets. The further biochemical and functional characterization of binding proteins was described above.

The invention permits the person skilled in the art to remove, from a chosen repertoire of polypeptides, those polypeptides which are incapable of binding to the target with the affinity specified in the claims. The invention permits the person skilled in the art to enrich a chosen repertoire of di-ubiquitin muteins which are functional and capable of binding to a given target.

EXAMPLES

The following Examples are provided for further illustration of the invention. The invention is particularly exemplified by particular ubiquitin muteins with binding capability to protein targets Her2, CD3, epCAM, or EGFR. The invention, however, is not limited thereto, and the following Examples merely show the practicability of the invention on the basis of the above description. For a complete disclosure of the invention reference is made also to the literature cited in the application which is incorporated completely into the application by reference.

Example 1. Identification of Binding Proteins

Library Construction and Cloning

Two ubiquitin moieties each comprising seven randomized amino acid positions were synthesized by triplet technology (MorphoSys Slonomics, Germany) to achieve a well-balanced amino acid distribution. A mixture of 19-amino acid coding premade double-stranded triplets (excluding cysteine) was used for the synthesis of the library. Both ubiquitin moieties were directly linked in head to tail orientation to result a protein of 152 amino acids with 14 randomized amino acid positions. The sequence of di-ubiquitin with 14 randomized positions is shown in SEQ ID NO: 3: MQIFVKTLTGKTITLEVEPSDTIENVKAKIQD-KEGIPPDQQXLXFAGKQLEDGRTLSDYNIQKESTLX-LXLXXXAAMQ IFVXTXTGKTITLEVEPSDTIEN-VKAKIQDKEGIPPDQQRLIWAGKQLEDGRTLSDYNI-XXXXXLHLVLRLRAA wherein X individually corresponds to an amino acid residue selected from S, Y, W, V, H, R, D, N, E, Q, G, K, F, T, A, L, I, or F.

The 14 randomized amino acids in the mutein correspond to positions R42, I44, H68, V70, R72, L73, R74, K82, L84, Q138, K139, E140, S141, and T142 of di-ubiquitin. The sequence of di-ubiquitin is shown in SEQ ID NO: 4: MQIFVKTLTGKTITLEVEPSDTIENVKAKIQDKEGIPP- DQQRLIFAGKQLEDGRTLSDYNIQKESTLHLVLRL-
RAAMQI FVKTLTGKTITLEVEPSDTIENVKAKIQDKE-
GIPPDQQRLIWAGKQLEDGRTLSDYNIQKESTLHLVL-
RLRAA.

The construct was ligated with a modified pCD87SA phagemid (herein referred to as pCD12) using standard methods known to a skilled person. The pCD12 phagemid comprises a modified torA leader sequence (deletion of amino acid sequence QPAMA) to achieve protein processing without additional amino acids at the N terminus. Aliquots of the ligation mixture were used for electroporation of *Escherichia coli* ER2738 (Lucigen). The library is referred to as SPIF. Unless otherwise indicated, established recombinant genetic methods were used, for example as described in Sambrook et al.

Targets.

Recombinant human target-Fc Chimera were purchased from R&D Systems. A DNA sequence encoding the extracellular domain of human EGFR (Uniprot Accession Number P00533; residues 1-645) or encoding the extracellular domain of human Her2 (Uniprot Accession Number P04626; residues 1-652) or encoding the extracellular domain of human epCAM (Uniprot Accession Number P16422; residues 1-265) or encoding human CD3 epsilon (Uniprot Accession Number P16422; all residues) was genetically fused with the Fc region of human IgG1 at the C-terminus.

TAT Phage Display Selection.

The SPIF library was enriched against the given protein target using TAT phage display as selection system. After transformation of competent bacterial ER2738 cells (Lucigene) with phagemid pCD12 carrying the SPIF library, phage amplification and purification was carried out using standard methods known to a skilled person. For selection the target protein was provided as Fc-fusion protein (Her2-Fc or EGFR-Fc or epCAM-Fc or CD3-Fc) immobilized on Dynabeads® Protein A or G. The target concentration during phage incubation varied from 200 nM (first round) to 50 nM (third round). Target phage complexes were magnetically separated from solution and washed several times. Target bound phages were eluted by trypsin. To deplete the phage library for Fc-binding variants a preselection of phages with immobilized Fc-fragment of IgG1 (Athens Research & Technology) was performed prior to round two and three.

To identify target specific phage pools, eluted and reamplified phages of each selection round were analysed by phage pool ELISA. Wells of a medium binding microtiter plate (Greiner bio-one) were coated at 2.5 µg/ml with Her2-Fc or EGFR-Fc or epCAM-Fc or CD3-Fc and Fc-fragment of IgG1 (5 µg/ml), respectively. Bound phages were detected using α-M13 HRP-conjugated antibody (GE Healthcare). Eluted and reamplified phages of round three showed specific binding to the target and were used subsequently for pool maturation by error prone PCR. Isolated phagemid pools served as template for error prone PCR (GeneMorph II Random Mutagenesis Kit, Agilent Technologies). The amplified pool of SPIF variants carrying now additional substitutions compared to the library positions was recloned into phagemid pCD12 and transformed into ER2738 for phage amplification and purification. The phages were again subjected to two rounds of panning as described above. The target was employed at a concentration of 5 nM and 1 nM in round one and two, respectively. For both rounds a preselection with Fc-fragment of IgG1 was performed. To analyze the matured and selected pools for specific target binding a phage pool ELISA was performed as described above.

Cloning of Target Binding Phage Pools into an Expression Vector.

Upon completion of the selection procedure the target specific DNA pools of maturation selection round one and two were amplified by PCR according to methods known in the art, cut with appropriate restriction nucleases and ligated into a derivative of the expression vector pET-28a (Merck, Germany) comprising a Strep-Tag II (IBA GmbH).

Single Colony Hit Analysis.

After transformation into BL21 (DE3) cells (Merck, Germany) kanamycin-resistant single colonies were grown. Expression of the target-binding modified ubiquitin was achieved by cultivation in 96 deep well plates (Genetix, UK) using auto induction medium (Studier, 2005). Cells were harvested and subsequently lysed. After centrifugation the resulting supernatants were screened by ELISA on plates coated with target and detected with Strep-Tactin® HRP Conjugate (IBA GmbH). As detecting reagent TMB-Plus (Biotrend, Germany) was used and the yellow colour was developed using 0.2 M $H_2SO_4$ solution and measured in a plate reader at 450 nm versus 620 nm.

Example 2. Solubility Analysis of the Proteins Encoded by the Library

The SPIF library was cloned into an expression vector using standard methods known to a skilled person. Expression of single clones was carried out in 96 deep well plates. Cells were cultivated over 16-18 h at 37° C. in auto induction medium. The pelleted cells were lysed using lysozyme and freeze-thaw-cycles. Soluble and insoluble fractions were separated by centrifugation. Proteins were recovered from pellets by addition of 8 M urea. Supernatants and resuspended pellets were analyzed by Criterion™ precast gels and the Criterion Stain Free imager (BioRad). For solubility analysis the Image Lab software from BioRad was used.

The solubility of the proteins encoded by the SPIF library and the expression level of all proteins encoded by the SPIF library was compared to the solubility and expression of the proteins encoded by four different di-ubiquitin based libraries. One library referred to as SPVF with randomized positions 6, 8, 62-66, 85, 87, 141-145 comprises two ubiquitin moieties (SEQ ID NO: 1) linked by a 3 amino acid linker (GIG). Further libraries with 14 different randomized positions between amino acids 46-66 and 122-142 of di-ubiquitin (SEQ ID NO: 4) and no linker between the two ubiquitin moieties (referred to as SPGO, SPOO, SPKK) were compared to SPIF.

TABLE 2

Libraries based on two ubiquitin moieties

| Library name | Linker | Positions substituted in di-ubiquitin (SEQ ID NO: 4) |
|---|---|---|
| SPIF | — | 42, 44, 68, 70, 72, 73, 74, 82, 84, 138-142 |
| SPVF | GIG | 6, 8, 62-66, 85, 87, 141-145 |
| SPGO | — | 14 selected from 53-63 and 123-137 |
| SPOO | — | 14 selected from 47-60 and 123-137 |
| SPKK | — | 14 selected from 46-66 and 122-142 |

Figure 2:
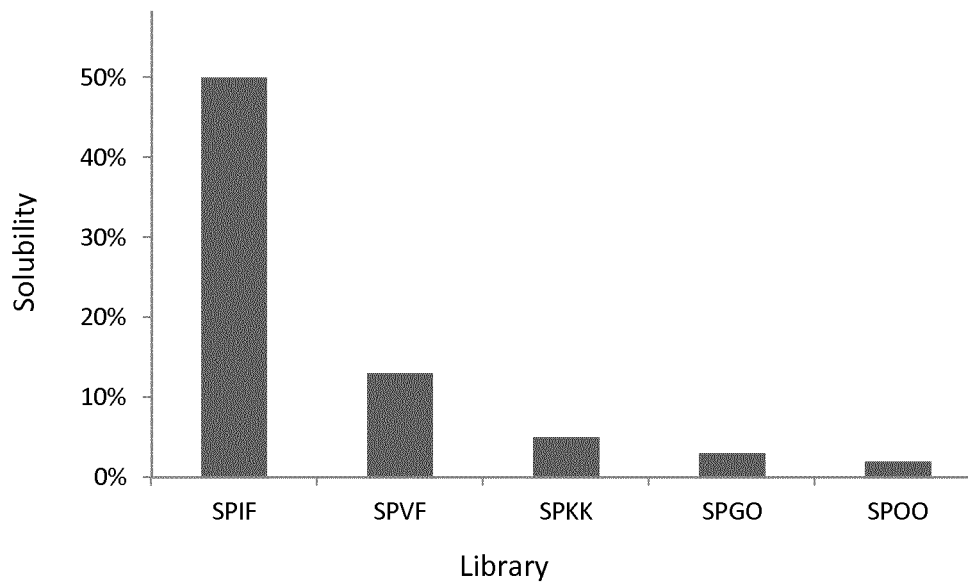
FIG. 2. Biochemical properties of the SPIF library
Figure 2:
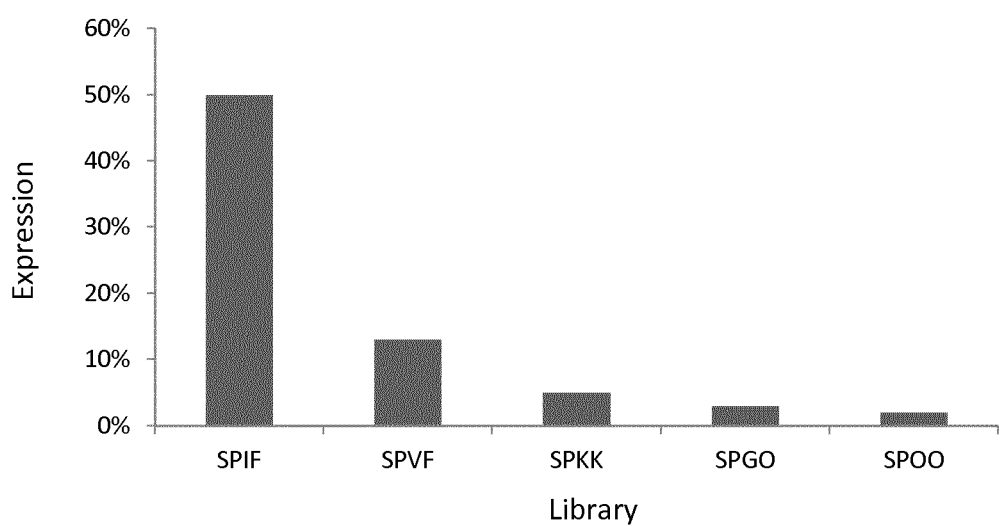

The solubility of the proteins encoded by the SPIF library was unexpected significantly enhanced compared to the SPVF library. All other libraries having different randomized positions than SPIF showed significantly lower levels of solubility of the proteins encoded by SPVF library, SPGO library, SPOO library, or SPKK library than those encoded by the SPIF library. "Enhanced solubility" may mean a higher proportion of a protein solute in a solvent as compared to another protein. It may also mean decreased protein aggregation or lower proportion of aggregated protein at a given protein concentration in a solvent, as compared to other proteins. Surprisingly, the expression level of all proteins encoded by the SPIF library is improved compared to the SPVF library, SPGO library, SPOO library, or SPKK library. All other libraries tested showed lower expression rates of encoded proteins (see FIG. 2 and Table 3).

TABLE 3

Comparison of solubility and expression level of different di-ubiquitin based libraries

| solubility and expression level | SPIF library | SPVF library | SPGO library | SPOO library | SPKK library |
|---|---|---|---|---|---|
| at least 70% soluble | 50 | 13 | 3 | 2 | 5 |
| at least 30% soluble | 24 | 14 | 2 | 1 | 7 |
| maximum 30% soluble | 25 | 61 | 35 | 9 | 39 |
| not soluble | 1 | 12 | 60 | 88 | 49 |
| Expression strong | 90 | 84 | 65 | 22 | 42 |
| Expression middle | 8 | 10 | 25 | 45 | 34 |
| Expression weak | 1 | 5 | 6 | 27 | 16 |
| no expression | 1 | 1 | 4 | 6 | 8 |

Example 3. Expression and Purification of Ubiquitin Muteins

Affilin molecules were subcloned to an expression vector using standard methods known to a skilled person, purified and analyzed as described below. All Affilin proteins were expressed and highly purified by affinity chromatography and gel filtration. After affinity chromatography purification a size exclusion chromatography (SE HPLC or SEC) has been performed using an Äkta system and a Superdex™ 200 HiLoad 16/600 column (GE Healthcare). The column has a volume of 120 ml and was equilibrated with 2 CV. The samples were applied with a flow rate of 1 ml/min purification buffer B. Fraction collection starts as the signal intensity reaches 10 mAU. Following SDS-PAGE analysis positive fractions were pooled and their protein concentrations were measured. Further analysis included SDS-PAGE, SE-HPLC and RP-HPLC. Protein concentrations were determined by absorbance measurement at 280 nm using the molar absorbent coefficient. RP chromatography (RP HPLC) has been performed using a Dionex HPLC system and a Vydac 214MS54 C4 (4.6×250 mm, 5 μm, 300 Å) column (GE Healthcare).

Example 4. Solubility Analysis of Binding Proteins

Supernatants and resuspended pellets were analyzed by NuPage Novex 4-12% Bis-Tris SDS gels and stained with Coomassie. Proteins were recovered from the pellets by addition of 8 M urea. All Affilin proteins tested displayed a high solubility of at least 80% solubility.

Example 5. Binding Proteins are Stable at High Temperatures

Thermal stability of the binding proteins of the invention was determined by Differential Scanning Fluorimetry (DSF). Each probe was transferred at concentrations of 0.1 μg/μL to a MicroAmp® Optical 384-well plate well plate, and SYPRO Orange dye was added at suitable dilution. A temperature ramp from 25 to 95° C. was programmed with a heating rate of 1° C. per minute (ViiA-7 Applied Biosystems). Fluorescence was constantly measured at an excitation wavelength of 520 nm and the emission wavelength at 623 nm (ViiA-7, Applied Biosystems). The midpoints of transition for the thermal unfolding (Tm, melting points) are shown for selected variants in Table 4.

Example 6. Analysis of Affinity to Targets

Figure 4:
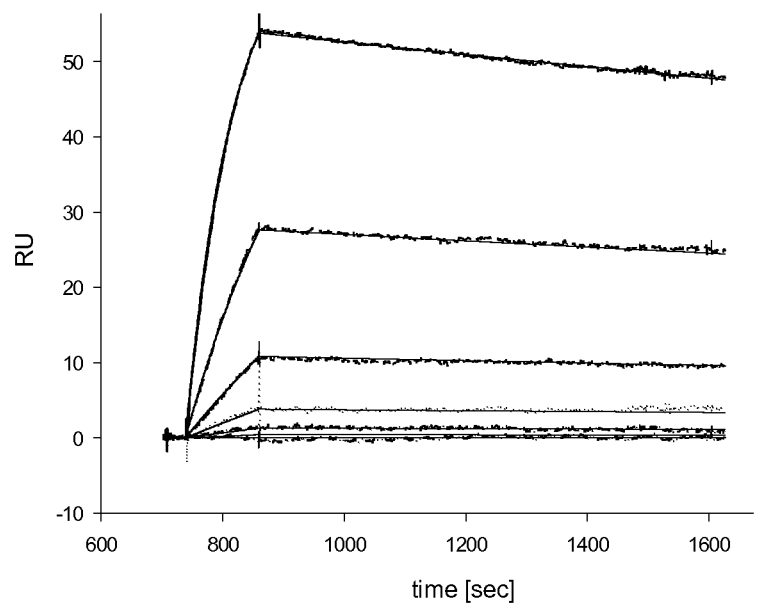
FIG. 4 shows results of an analysis of binding proteins for protein targets of di-ubiquitin muteins via label-free interaction assays using SPR. Different concentrations of Affilin proteins were analyzed for binding to protein targets of di-ubiquitin (SEQ ID NO: 4) immobilized on a chip (Biacore) to analyze the interaction between Affilin and protein targets of di-ubiquitin.
Figure 4:
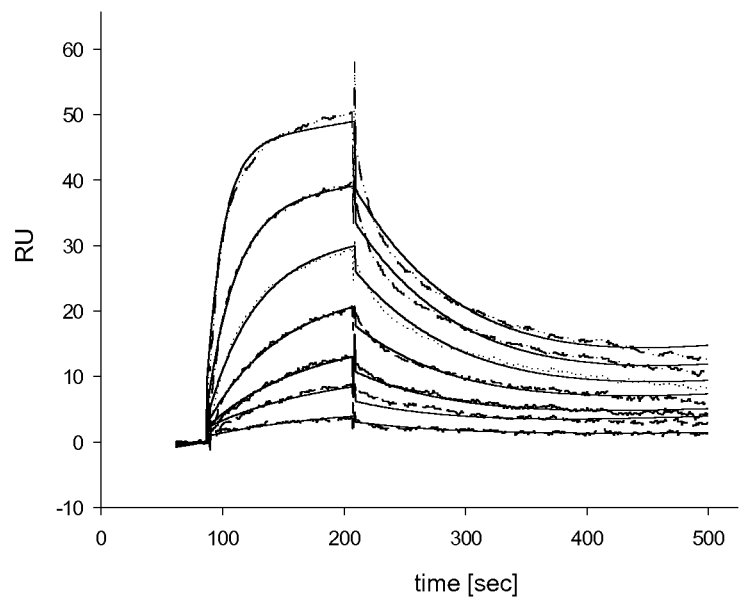
Figure 4:
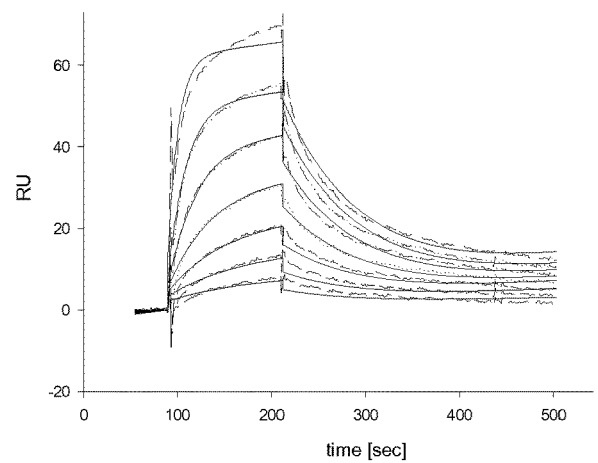
Figure 4:
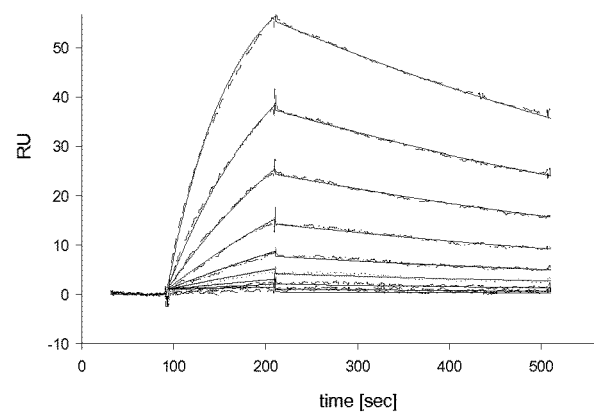

A CM5 sensor chip (GE Healthcare) was equilibrated with Surface Plasmon Resonance (SPR) running buffer. Surface-exposed carboxylic groups were activated by passing a mixture of EDC and NHS to yield reactive ester groups. 700-1500 RU "target"-Fc (on-target) were immobilized on a flow cell, IgG-Fc (off-target) was immobilized on another flow cell at a ratio of 1:3 (hIgG-Fc:Target) to the target. Injection of ethanolamine after target immobilization removes non-covalently bound target. Upon target binding, protein analyte was accumulated on the surface increasing the refractive index. This change in the refractive index was measured in real time and plotted as response or resonance units (RU) versus time. The analytes were applied to the chip in serial dilutions with a flow rate of 30 μl/min. The association was performed for 30 seconds and the dissociation for 60 seconds. After each run, the chip surface was regenerated with 30 μl regeneration buffer and equilibrated with running buffer. A dilution series of Trastuzumab served as positive control, whereas a dilution series of unmodified ubiquitin represents the negative control. The control samples were applied to the matrix with a flow rate of 30 μl/min, while they associate for 60 seconds and dissociate for 120 seconds. Regeneration and re-equilibration were performed as previously mentioned. Binding studies were carried out by the use of the Biacore® 3000 (GE Healthcare); data evaluation was operated via the BIAevaluation 3.0 software, provided by the manufacturer, by the use of the Langmuir 1:1 model (RI=0). Results of binding to specific targets are shown in FIG. 4 and in Table 4. Evaluated dissociation constants ($K_D$) were standardized against off-target and indicated.

Table 4 shows biochemical characterization of binding Affilin molecules, in particular binding affinities ($K_D$) for the binding proteins, for example, Her2, EpCAM, EGFR, and CD3, as obtained from SPR (Affinity to target in nM; fourth column of the table) and temperature stability is shown (Tm in ° C.; fifth column of the table).

| SEQ ID | Affilin- | Target specificity | Affinity to target (nM) | Tm (° C.) |
|---|---|---|---|---|
| 5 | 142437 | Her2 | 29.6 | 62.7 |
| 6 | 142672 | Her2 | 4.44 | 68.7 |
| 7 | 144637 | Her2 | 0.35 | 53.66 |
| 8 | 144636 | Her2 | 0.49 | 55.12 |
| 9 | 144635 | Her2 | 0.77 | 46.16 |
| 10 | 144634 | Her2 | 0.72 | 46.19 |
| 11 | 144633 | Her2 | 0.38 | 56.25 |
| 12 | 144632 | Her2 | 0.87 | 60.33 |
| 13 | 144631 | Her2 | 0.64 | 49.73 |
| 14 | 142679 | Her2 | 1.27 | 64.3 |
| 15 | 142658 | Her2 | 1.97 | 65.9 |
| 16 | 142654 | Her2 | 0.65 | 68.5 |
| 17 | 142653 | Her2 | 0.75 | 47.6 |
| 18 | 142645 | Her2 | 8.11 | 48.7 |
| 19 | 142628 | Her2 | 0.39 | 62.4 |
| 20 | 142620 | Her2 | 0.72 | 66 |
| 21 | 142618 | Her2 | 75.7 | 67.4 |

-continued

| SEQ ID | Affilin- | Target specificity | Affinity to target (nM) | Tm (° C.) |
|---|---|---|---|---|
| 22 | 142617 | Her2 | 1.06 | 43.99 |
| 23 | 142609 | Her2 | 0.91 | 74.3 |
| 24 | 142451 | Her2 | 1.16 | 42 |
| 25 | 142441 | Her2 | 3.38 | 68.5 |
| 26 | 142439 | Her2 | 4.17 | 62.4 |
| 27 | 141931 | Her2 | 74.2 | 67.4 |
| 28 | 141926 | Her2 | 8.9 | 73.8 |
| 29 | 141869 | Her2 | 44 | 74.3 |
| 30 | 141890 | Her2 | 25.5 | 64.8 |
| 31 | 141912 | Her2 | 100 | 72.93 |
| 32 | 141935 | Her2 | 88.9 | 64.4 |
| 33 | 142465 | Her2 | 21.6 | 82 |
| 34 | 142655 | Her2 | 510 | 66.6 |
| 35 | 142418 | Her2 | 1.66 | 69.2 |
| 36 | 142627 | Her2 | 9.73 | N.D. |
| 37 | 141975 | Her2 | 39.4 | 72.53 |
| 39 | 144160 | CD3 | 46.5 | 59.55 |
| 40 | 143488 | EpCAM | 150 | 71.4 |
| 41 | 143283 | EpCAM | 31.8 | 67.5 |
| 42 | 142265 | EGFR | 620 | 66.5 |

Figure 5:
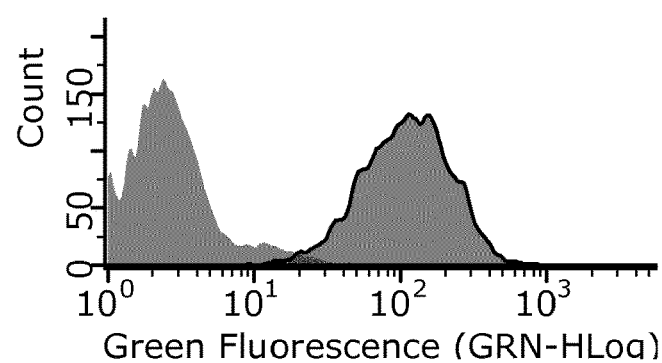
FIG. 5 shows a functional characterization of binding molecules of the invention.
Figure 5:
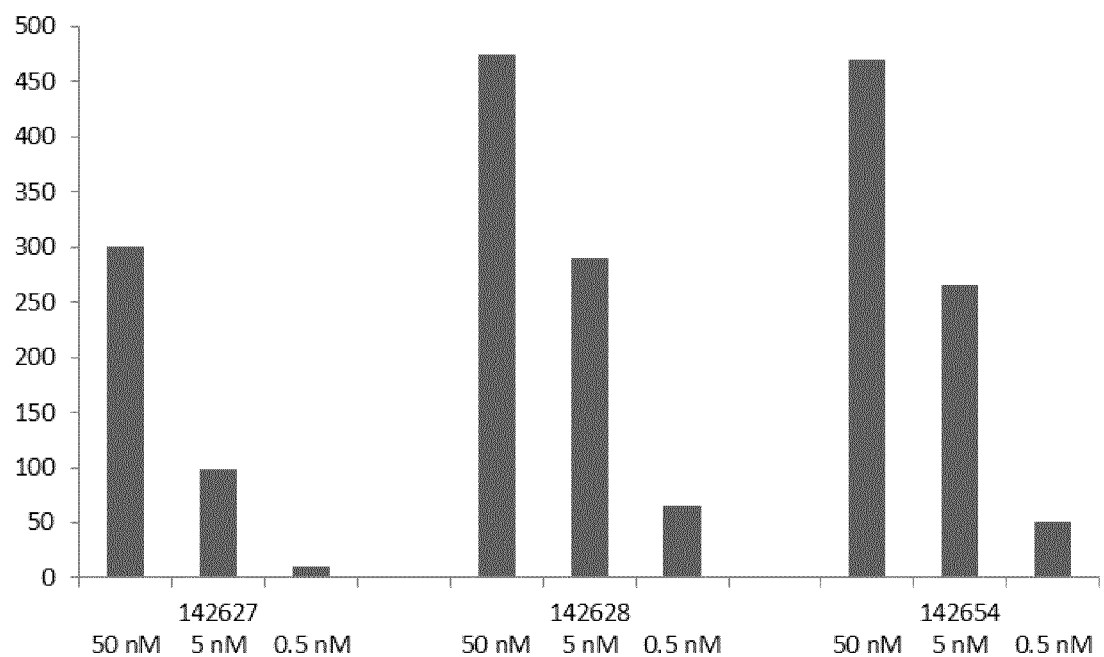
Figure 5C:
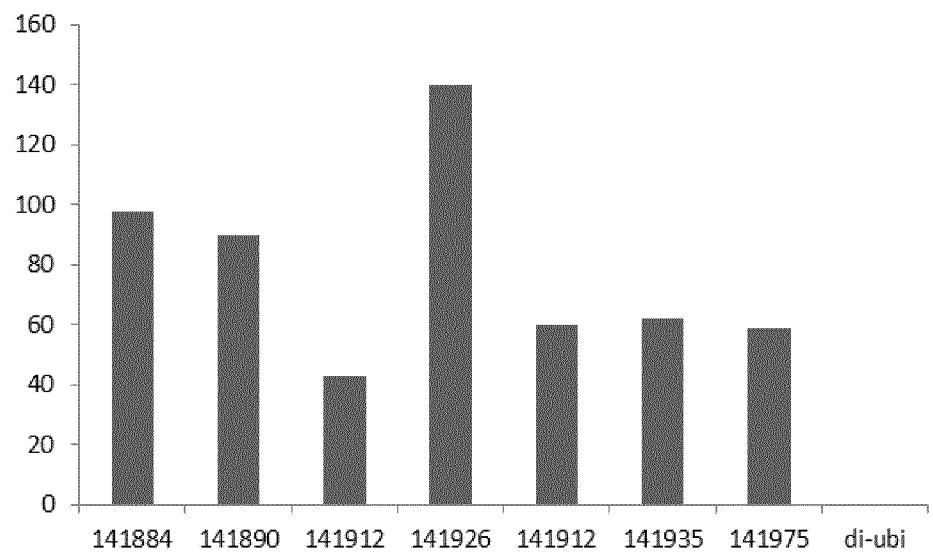
Figure 6:
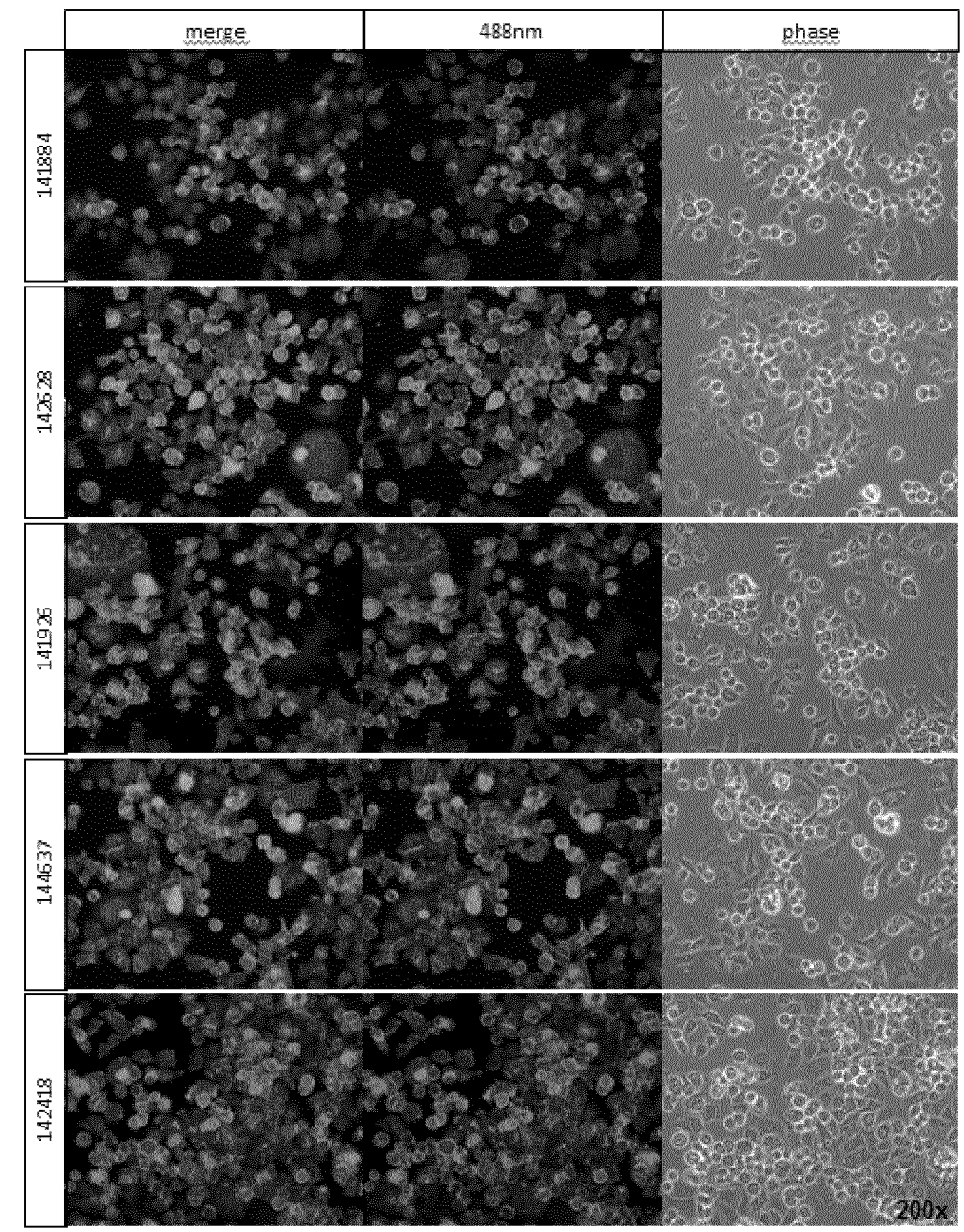
FIG. 6. Binding analysis of Her2 binding proteins on Her2-overexpressing SkBr3-cells by immunofluorescence cell staining. All Affilin proteins show a strong binding of 50 nM on the SkBr3-cells, whereas di-ubiquitin shows no binding.

Example 7. Functional Characterization: Binding to Cell Surface Expressed Targets Additional functional characterization was performed by target binding analysis with Her2 overexpressing cells or EGFR overexpressing cells. Different concentrations of specific Affilin molecules were tested. Her2 cell target binding or EGFR cell target binding was confirmed, as shown in the Figures. Flow cytometry was used to analyze the interaction of Her2 binding proteins or EGFR binding proteins with surface-exposed Her2. Her2 overexpressing human mammary gland adenocarcinoma-derived SkBr3 cells, Her2 overexpressing transfected CHO-K1 cells or EGFR overexpressing transfected CHO-K1 cells, Her2 non-expressing human embryonic kidney cell line HEK/293 or EGFR non-expressing cell line HEK/293 and empty vector control CHO-K1 cells were used. The anti-Her2 monoclonal antibody Trastuzumab or anti-EGFR monoclonal antibody Cetuximab were used as positive controls, respectively. Results are summarized in FIG. 5 and FIG. 6.

Cells were trypsinized and resupended in medium containing FCS, washed and stained in pre-cooled FACS blocking buffer. A cell concentration of $2\times10^6$ cells/ml was prepared for cell staining and filled into a 96 well plate (Greiner) in triplicate for each cell line. Different concentrations of Affilin proteins were added to Her2 or EGFR overexpressing and control cells in several experiments as indicated in the figures. After 45 min the supernatants were removed and 100 μl/well rabbit anti-Strep antibody (obtained from GenScript; A00626), 1:300 diluted in FACS blocking buffer were added. After removal of the primary antibody goat anti-human IgG Alexa Fluor 488 antibody (obtained from Invitrogen; A11008) was applied in a 1:1000 dilution. Flow cytometry measurement was conducted on the Guava easyCyte 5HT device from Merck-Millipore at excitation wavelength 488 nm and emission wavelength 525/30 nm. Comparable amounts of clone 139090 were used as negative control in the experiments.

Example 8. Functional Characterization: Binding to Cell Surface Expressed Her2

Binding of proteins of the invention on cells exogenously expressing human Her2 was confirmed by immunocytochemistry and fluorescence microscopy. 50 nM of Affilin-141884, Affilin-142628, Affilin-141926, Affilin-144637, Affilin-142418 and Affilin-144567 were tested on Her2-expressing SkBr3 cells and the negative control cell line HEK/293. Cells were seeded with a concentration of $1\times10^5$ cells/ml in Lab-Tek® Chamber-Slides (Sigma-Aldrich). After cultivation over 72 h the cells were fixed with methanol (5 min., 20° C.), followed by blocking (5% Fetal Horse Serum in PBS, 1 h) and incubation with 50 nM Affilin for 45 min at rt. Affilin binding was detected by an incubation of rabbit-anti-Strep-Tag-antibody (1:500) for 1 h and subsequent incubation with anti-rabbit-IgG-Alexa488-antibody (1:1000) for 1 h. The nuclei were stained with 4 μg/ml DAPI. All incubation steps were at room temperature.

Example 9. Functional Characterization: Her2 Binding Proteins Bind to Extracellular Her2 Expressed on Tissue Cells Derived from Tumors Tissue sections of SKOV-3-tumor, lung, liver, heart muscle and ovary were used to analyze the binding proteins of the invention by immunohistochemistry and fluorescence microscopy. Tissue slices were fixed with ice-cold Acetone for 10 min, followed by blocking and incubation with different concentrations (20 nM and 50 nM) of Affilin-141884 and Affilin-142628 and an equal amount of di-ubiquitin clone 139090 as negative or 10 nM Trastuzumab as positive control for 1 h. After washing with PBS the tissue was incubated with rabbit anti-Strep-Tag antibody (1:500) for 1 h at room temperature, followed by an incubation with goat anti-rabbit Alexa488 (1:1000) or goat anti-human Alexa594 (1:1000) secondary antibody. Nuclei of cells were visualized with DAPI. Chamber slides were dissembled and the glass slides covered with Mowiol and a cover glass. Slices were imaged at a Zeiss Axio Scope.A1 microscope and images were processed using standard software packages. FIG. 7 show the specific binding of Her2 Affilin molecules on SKOV-3-tumor-slices compared to the non-binding protein clone 139090. No binding on lung, liver, heart muscle and ovarian tissues was observed.

Example 10. Binding Proteins Bind to Extracellular Target Expressed on Tumor Cells A431 cells are derived from epidermoid carcinoma and are known for the high expression levels of EGFR. A431 cells were seeded in Lab-Tek® Chamber Slides (Sigma-Aldrich) and incubated for 2 days at 37° C., 5% $CO_2$. Cells were fixed with 3% paraformaldehyde for 10 minutes at RT, washed with PBS and subsequently blocked with blocking solution (BS, 3% BSA+0.1% Triton-X100) for 30 min at 4° C. Cells were then incubated with 500 nM binding protein Affilin-142265) or 10 nM Cetuximab as control for 1 h at 4° C. Unmodified ubiquitin (referred to as clone 139090) served as negative control. After washing with PBS cells were incubated with rabbit anti-Strep-antibody (1:500) for 1 h at 4° C. Cells were then incubated with donkey anti-Rabbit Alexa488 (1:1000) or goat anti-Human Alexa 594 (1:1000) secondary antibodies followed by visualization of cell nuclei with DAPI. Chamber slides were dissembled and the glass slide was covered with Mowiol and a cover glass. Cells were imaged at a Zeiss Axio Scope.A1 microscope and images were processed using standard software packages. The staining of A431 tumor cells expressing EGFR confirms binding of Affilin 142265 to extracellular EGFR.

The invention claimed is:

1. A method for generating a di-ubiquitin mutein that binds to a given target with a dissociation constant (KD) of at least 1000 nM, said method comprising:
   a. subjecting a nucleic acid molecule encoding a di-ubiquitin having the amino acid sequence as set forth in SEQ ID NO: 4 to mutagenesis in positions encoding at least 12 amino acids selected from the group consisting of R42, I44, H68, V70, R72, L73, R74, K82, L84, Q138, K139, E140, S141, and T142 of SEQ ID NO: 4 to generate one or more mutated nucleic acid molecules encoding one or more di-ubiquitin muteins;
   b. expressing the one or more mutated nucleic acid molecules in a suitable expression system;
   c. selecting and/or isolating at least one of the one or more mutated nucleic acid molecules that encodes a di-ubiquitin mutein that has a dissociation constant (KD) of at least 1000 nM for the given target, wherein the amino acid sequence of said di-ubiquitin mutein encoded by the at least one mutated nucleic acid molecule is between 85% and 92% identical to SEQ ID NO: 4 and has an affinity for the target that is at least 10-fold higher than does a di-ubiquitin having the amino acid sequence as set forth in SEQ ID NO: 4; and
   d. expressing the selected and/or isolated at least one mutated nucleic acid molecules in a host cell,
   whereby a di-ubiquitin molecule that binds to the given target with a dissociation constant (KD) of at least 1000 nM is generated.

2. The method of claim 1, wherein the target is a peptide, a protein, or a domain of a protein.

3. The method of claim 2, wherein the target is selected from the group consisting of Her2, EGFR, CD3, and epCAM.

4. A nucleic acid library encoding a plurality of di-ubiquitin muteins, wherein the plurality of di-ubiquitin muteins comprise substitutions of 12-14 amino acid residues selected from the group consisting of amino acid positions R42, I44, H68, V70, R72, L73, R74, K82, L84, Q138, K139, E140, S141, and T142 of SEQ ID NO: 4.

5. A binding protein comprising an amino acid sequence that is between 85% and 92% identical to SEQ ID NO: 4, wherein the binding protein comprises substitutions of 12-14 amino acids at a position selected from the group consisting of R42, I44, H68, V70, R72, L73, R74, K82, L84, Q138, K139, E140, S141, and T142 of SEQ ID NO: 4 and has a specific binding affinity for a target that is at least 10-fold higher than does a di-ubiquitin comprising SEQ ID NO: 4.

6. The binding protein of claim 5, wherein the amino acid sequence of the binding protein further comprises 1-6 additional amino acid substitutions as compared to SEQ ID NO: 4.

7. The binding protein of claim 5, wherein the binding protein has a specific binding affinity of at least 10 nM for a target selected from the group consisting of a peptide, a protein, and a domain of a protein.

8. The binding protein of claim 7, wherein the amino acid sequence of the binding protein is selected from the group consisting of SEQ ID NOs: 5-42.

9. The binding protein of claim 7, wherein the binding protein is conjugated to or fused to at least one additional molecule, and further wherein the at least one additional molecule is selected from the group consisting of a pharmacokinetic modulating moiety, a therapeutically active component, and a diagnostic component.

10. The binding protein of claim 7, wherein the binding protein has a specific binding affinity of at least 100 nM for the target.

11. The binding protein of claim 7, wherein the binding protein has a specific binding affinity of at least 700 nM for the target.

12. The binding protein of claim 7, wherein the target is selected from the group consisting of Her2, EGFR, CD3, and EpCAM.

13. The binding protein of claim 9, wherein the pharmacokinetic modulating moiety is selected from the group consisting of a polyethylene glycol, a human serum albumin, an albumin-binding peptide, an immunoglobulin molecule or a fragment thereof, and a polysaccharide.

14. The binding protein of claim 9, wherein the therapeutically active component is selected from the group consisting of a monoclonal antibody or a fragment thereof, a cytokine, a chemokine, a cytotoxic compound, an enzyme, and a radionuclide.

15. The binding protein of claim 9, wherein the diagnostic component is selected from the group consisting of a fluorescent compound, a photosensitizer, a tag, an enzyme, and a radionuclide.

16. A nucleic acid molecule encoding the binding protein of claim 5.

17. A vector comprising the nucleic acid molecule of claim 16.

18. A host cell or a non-human host comprising the binding protein of claim 5 or a nucleic acid encoding the binding protein of claim 5.

19. A composition comprising the binding protein of claim 5 and a pharmaceutically acceptable carrier.

20. A method for identifying a di-ubiquitin mutein with an affinity for a target that is at least 10-fold higher than that of a di-ubiquitin comprising SEQ ID NO: 4 for the same target, the method comprising screening the nucleic acid library of claim 4 and identifying a di-ubiquitin mutein that binds to the target and has an affinity for the target that is at least 10-fold higher than the di-ubiquitin comprising the amino acid sequence as set forth in SEQ ID NO: 4.

21. The method of claim 20, comprising:
(a) expressing the nucleic acid library of claim 4 on the surface of a host cell, wherein the nucleic acid library of claim 4 encodes a plurality of di-ubiquitin muteins, and further wherein the plurality of di-ubiquitin muteins comprise substitutions of 12-14 amino acid residues selected from the group consisting of amino acid positions R42, I44, H68, V70, R72, L73, R74, K82, L84, Q138, K139, E140, S141, and T142 of SEQ ID NO: 4;
(b) contacting the members of the expressed nucleic acid library of claim 4 with a target;
(c) identifying one or more members of the expressed nucleic acid library of claim 4 that bind to the target; and
(d) screening the one or more members of the expressed nucleic acid library of claim 4 that bind to the target to identify a di-ubiquin mutein that binds to the target with a specific binding affinity of at least 1000 nM.

22. The method of claim 21, further comprising isolating a member of the expressed library that binds to the target with a specific binding affinity of at least 1000 nM.

23. A method for diagnosing or treating a disease or disorder associated with expression of a target to which the binding protein of claim 5 binds, the method comprising administering to a subject in need thereof a diagnostically or therapeutically effective dose of the binding protein of claim 5.

24. The method of claim 23, wherein the disease or disorder is cancer or an autoimmune disorder.

* * * * *

SEQUENCE LISTING

<160> NUMBER OF SEQ ID NOS: 45

<210> SEQ ID NO 1
<211> LENGTH: 76
<212> TYPE: PRT
<213> ORGANISM: Artificial sequence
<220> FEATURE:
<223> OTHER INFORMATION: Artificially synthesized wildtype ubiquitin

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 76
<212> TYPE: PRT
<213> ORGANISM: Artificial sequence
<220> FEATURE:
<223> OTHER INFORMATION: Artificially synthesized ubiquitin reference

<400> SEQUENCE: 2

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Ala
65                  70                  75

<210> SEQ ID NO 3
<211> LENGTH: 152
<212> TYPE: PRT
<213> ORGANISM: Artificial sequence
<220> FEATURE:
<223> OTHER INFORMATION: Artificially synthesized ubiquitin reference
<220> FEATURE:
<221> NAME/KEY: SITE
<222> LOCATION: (42)..(42)
<223> OTHER INFORMATION: Xaa can be any naturally occurring amino acid
<220> FEATURE:
<221> NAME/KEY: SITE
<222> LOCATION: (44)..(44)
<223> OTHER INFORMATION: Xaa can be any naturally occurring amino acid
<220> FEATURE:
<221> NAME/KEY: SITE
<222> LOCATION: (68)..(68)
<223> OTHER INFORMATION: Xaa can be any naturally occurring amino acid
<220> FEATURE:
<221> NAME/KEY: SITE
<222> LOCATION: (70)..(70)
<223> OTHER INFORMATION: Xaa can be any naturally occurring amino acid
<220> FEATURE:
<221> NAME/KEY: SITE
<222> LOCATION: (72)..(74)
<223> OTHER INFORMATION: Xaa can be any naturally occurring amino acid -continued

```
<220> FEATURE:
<221> NAME/KEY: SITE
<222> LOCATION: (82)..(82)
<223> OTHER INFORMATION: Xaa can be any naturally occurring amino acid
<220> FEATURE:
<221> NAME/KEY: SITE
<222> LOCATION: (84)..(84)
<223> OTHER INFORMATION: Xaa can be any naturally occurring amino acid
<220> FEATURE:
<221> NAME/KEY: SITE
<222> LOCATION: (138)..(142)
<223> OTHER INFORMATION: Xaa can be any naturally occurring amino acid

<400> SEQUENCE: 3

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Xaa Leu Xaa Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu Xaa Leu Xaa Leu Xaa Xaa Xaa Ala Ala Met Gln Ile Phe
65                  70                  75                  80

Val Xaa Thr Xaa Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Xaa Xaa Xaa Xaa Xaa Leu His
    130                 135                 140

Leu Val Leu Arg Leu Arg Ala Ala
145                 150

<210> SEQ ID NO 4
<211> LENGTH: 152
<212> TYPE: PRT
<213> ORGANISM: Artificial sequence
<220> FEATURE:
<223> OTHER INFORMATION: Artificially synthesized di-ubiquitin reference
      clone 139090

<400> SEQUENCE: 4

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Ala Ala Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125
```

Gly Arg Thr Leu Ser Asp Tyr Asn Ile Gln Lys Glu Ser Thr Leu His
        130                 135                 140

Leu Val Leu Arg Leu Arg Ala Ala
145                 150

<210> SEQ ID NO 5
<211> LENGTH: 152
<212> TYPE: PRT
<213> ORGANISM: Artificial sequence
<220> FEATURE:
<223> OTHER INFORMATION: Artificially synthesized Affilin-142437

<400> SEQUENCE: 5

Met Gln Ile Phe Val Lys Thr Leu Thr Gly Lys Thr Ile Thr Leu Glu
1               5                   10                  15

Val Glu Pro Ser Asn Thr Ile Glu Asn Val Lys Ala Lys Ile Gln Asp
            20                  25                  30

Lys Glu Gly Thr Pro Pro Asp Gln Gln Thr Leu Ala Phe Ala Gly Lys
        35                  40                  45

His Leu Glu Asp Gly Arg Thr Leu Ser Asp Tyr Asn Ile Gln Lys Glu
    50                  55                  60

Ser Thr Leu Trp Leu Tyr Leu Thr Trp Asn Ala Ala Met Arg Ile Phe
65                  70                  75                  80

Val Thr Thr His Thr Gly Lys Asn Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 6
<211> LENGTH: 152
<212> TYPE: PRT
<213> ORGANISM: Artificial sequence
<220> FEATURE:
<223> OTHER INFORMATION: Artificially synthesized Affilin-142672

<400> SEQUENCE: 6

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Thr Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Leu Thr Asp Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp

```
                    115                 120                 125
Gly Arg Thr Leu Ser Asp Tyr Asn Ile Arg Gly Trp Ser Leu Leu His
            130                 135                 140

Leu Val Leu Arg Leu Arg Ala Ala
145                 150

<210> SEQ ID NO 7
<211> LENGTH: 152
<212> TYPE: PRT
<213> ORGANISM: Artificial sequence
<220> FEATURE:
<223> OTHER INFORMATION: Artificially synthesized Affilin-144637

<400> SEQUENCE: 7

Met Gln Ile Phe Val Lys Thr Leu Thr Gly Lys Thr Ile Thr Leu Glu
1               5                   10                  15

Val Glu Pro Ser Asp Thr Thr Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Tyr Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Asp Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 8
<211> LENGTH: 152
<212> TYPE: PRT
<213> ORGANISM: Artificial sequence
<220> FEATURE:
<223> OTHER INFORMATION: Artificially synthesized Affilin-144636

<400> SEQUENCE: 8

Met Gln Ile Phe Val Lys Thr Leu Thr Gly Lys Thr Ile Thr Leu Glu
1               5                   10                  15

Val Glu Pro Ser Asp Thr Thr Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Tyr Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110
```

```
Pro Pro Asp Gln Gln Arg Leu Ile Trp Ala Gly Lys Gln Leu Glu Asp
            115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 9
<211> LENGTH: 152
<212> TYPE: PRT
<213> ORGANISM: Artificial sequence
<220> FEATURE:
<223> OTHER INFORMATION: Artificially synthesized Affilin-144635

<400> SEQUENCE: 9

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Met
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65              70                  75                  80

Val Thr Thr His Thr Gly Lys Thr Ile Thr Leu Asp Val Glu Pro Ser
            85                  90                  95

Asp Thr Ile Glu Asn Val Lys Ala Lys Ile Gln Asp Lys Glu Gly Ile
        100                 105                 110

Pro Pro Asp Gln Gln Arg Leu Ile Trp Ala Gly Met Gln Leu Glu Asp
            115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 10
<211> LENGTH: 152
<212> TYPE: PRT
<213> ORGANISM: Artificial sequence
<220> FEATURE:
<223> OTHER INFORMATION: Artificially synthesized Affilin-144634

<400> SEQUENCE: 10

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65              70                  75                  80

Val Thr Thr His Thr Gly Lys Thr Ile Thr Leu Asp Val Glu Pro Ser
            85                  90                  95

Asp Thr Ile Glu Asn Val Lys Ala Lys Ile Gln Asp Lys Glu Gly Ile
        100                 105                 110
```

```
Pro Pro Asp Gln Gln Arg Leu Ile Trp Ala Gly Met Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 11
<211> LENGTH: 152
<212> TYPE: PRT
<213> ORGANISM: Artificial sequence
<220> FEATURE:
<223> OTHER INFORMATION: Artificially synthesized Affilin-144633

<400> SEQUENCE: 11

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Tyr Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Asp Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 12
<211> LENGTH: 152
<212> TYPE: PRT
<213> ORGANISM: Artificial sequence
<220> FEATURE:
<223> OTHER INFORMATION: Artificially synthesized Affilin-144632

<400> SEQUENCE: 12

Met Gln Ile Phe Val Lys Thr Leu Thr Gly Lys Thr Ile Thr Leu Glu
1               5                   10                  15

Val Glu Pro Ser Asp Thr Thr Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
```

Pro Pro Asp Gln Gln Arg Leu Ile Trp Ala Gly Lys Gln Leu Glu Asp
            115                 120                 125

Gly Arg Thr Leu Ser Asp Tyr Asn Ile Ser Glu Trp Ala Ile Leu His
        130                 135                 140

Leu Val Leu Arg Leu Arg Ala Ala
145                 150

<210> SEQ ID NO 13
<211> LENGTH: 152
<212> TYPE: PRT
<213> ORGANISM: Artificial sequence
<220> FEATURE:
<223> OTHER INFORMATION: Artificially synthesized Affilin-144631

<400> SEQUENCE: 13

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Asp Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 14
<211> LENGTH: 152
<212> TYPE: PRT
<213> ORGANISM: Artificial sequence
<220> FEATURE:
<223> OTHER INFORMATION: Artificially synthesized Affilin-142679

<400> SEQUENCE: 14

Met Gln Ile Phe Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Ser Glu Trp Ala Ile Leu His
        130                 135                 140

Leu Val Leu Arg Leu Arg Ala Ala
145                 150

<210> SEQ ID NO 15
<211> LENGTH: 152
<212> TYPE: PRT
<213> ORGANISM: Artificial sequence
<220> FEATURE:
<223> OTHER INFORMATION: Artificially synthesized Affilin-142658

<400> SEQUENCE: 15

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Thr Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Ser Glu Trp Ala Ile Leu Gln
        130                 135                 140

Leu Val Leu Arg Leu Arg Ala Ala
145                 150

<210> SEQ ID NO 16
<211> LENGTH: 152
<212> TYPE: PRT
<213> ORGANISM: Artificial sequence
<220> FEATURE:
<223> OTHER INFORMATION: Artificially synthesized Affilin-142654

<400> SEQUENCE: 16

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                85                  90                  95

```
Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 17
<211> LENGTH: 152
<212> TYPE: PRT
<213> ORGANISM: Artificial sequence
<220> FEATURE:
<223> OTHER INFORMATION: Artificially synthesized Affilin-142653

<400> SEQUENCE: 17

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                85                  90                  95

Asp Ser Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 18
<211> LENGTH: 152
<212> TYPE: PRT
<213> ORGANISM: Artificial sequence
<220> FEATURE:
<223> OTHER INFORMATION: Artificially synthesized Affilin-142645

<400> SEQUENCE: 18

Met Gln Ile Phe Val Lys Thr Leu Thr Asp Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
```

```
                    85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Thr Asp Tyr Asn Ile Ser Glu Trp Ala Ile Leu His
        130                 135                 140

Leu Val Leu Arg Leu Arg Ala Ala
145                 150

<210> SEQ ID NO 19
<211> LENGTH: 152
<212> TYPE: PRT
<213> ORGANISM: Artificial sequence
<220> FEATURE:
<223> OTHER INFORMATION: Artificially synthesized Affilin-142628

<400> SEQUENCE: 19

Met Gln Ile Phe Val Lys Thr Leu Thr Gly Lys Thr Ile Thr Leu Glu
1               5                   10                  15

Val Glu Pro Ser Asp Thr Thr Glu Asn Val Lys Ala Lys Ile Gln Asp
                20                  25                  30

Lys Glu Gly Ile Pro Pro Asp Gln Gln Thr Leu Ala Phe Val Gly Lys
            35                  40                  45

Gln Leu Glu Asp Gly Arg Thr Leu Ser Asp Tyr Asn Ile Gln Lys Glu
        50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Asp Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Ser Glu Trp Ala Ile Leu His
        130                 135                 140

Leu Val Leu Arg Leu Arg Ala Ala
145                 150

<210> SEQ ID NO 20
<211> LENGTH: 152
<212> TYPE: PRT
<213> ORGANISM: Artificial sequence
<220> FEATURE:
<223> OTHER INFORMATION: Artificially synthesized Affilin-142620

<400> SEQUENCE: 20

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Val Lys Ile Gln Asp
                20                  25                  30

Lys Glu Gly Ile Pro Pro Asp Gln Gln Thr Leu Ala Phe Val Gly Lys
            35                  40                  45

Gln Leu Glu Asp Gly Arg Thr Leu Ser Asp Tyr Asn Ile Gln Lys Glu
        50                  55                  60

Ser Thr Leu Trp Leu Tyr Leu Thr Trp Tyr Ala Ala Met Arg Ile Phe
65                  70                  75                  80
```

Val Thr Thr His Thr Gly Lys Thr Ile Thr Leu Glu Val Glu Pro Ser
            85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 21
<211> LENGTH: 152
<212> TYPE: PRT
<213> ORGANISM: Artificial sequence
<220> FEATURE:
<223> OTHER INFORMATION: Artificially synthesized Affilin-142618

<400> SEQUENCE: 21

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Lys Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Gln Ile Phe
65                  70                  75                  80

Val Thr Thr His Thr Gly Lys Thr Ile Thr Leu Glu Val Glu Pro Ser
            85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 22
<211> LENGTH: 152
<212> TYPE: PRT
<213> ORGANISM: Artificial sequence
<220> FEATURE:
<223> OTHER INFORMATION: Artificially synthesized Affilin-142617

<400> SEQUENCE: 22

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

```
Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Ser Asp Gln Gln Arg Leu Ile Trp Ala Gly Lys Gln Leu Glu Asp
        115                 120                 125

Gly Arg Ala Leu Ser Asp Tyr Asn Ile Ser Glu Trp Ala Ile Leu His
    130                 135                 140

Leu Val Leu Arg Leu Arg Ala Ala
145                 150

<210> SEQ ID NO 23
<211> LENGTH: 152
<212> TYPE: PRT
<213> ORGANISM: Artificial sequence
<220> FEATURE:
<223> OTHER INFORMATION: Artificially synthesized Affilin-142609

<400> SEQUENCE: 23

Met Gln Ile Phe Val Lys Thr Leu Thr Gly Asn Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Pro Arg Leu Arg Ala Ala
145                 150

<210> SEQ ID NO 24
<211> LENGTH: 152
<212> TYPE: PRT
<213> ORGANISM: Artificial sequence
<220> FEATURE:
<223> OTHER INFORMATION: Artificially synthesized Affilin-142451

<400> SEQUENCE: 24

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
```

```
                65                  70                  75                  80
Val Thr Thr His Thr Gly Lys Thr Ile Thr Leu Glu Val Glu Pro Thr
                    85                  90                  95

Asp Thr Ile Glu Asn Val Lys Ala Lys Ile Gln Asp Lys Glu Gly Ile
            100                 105                 110

Pro Pro Asp Gln Gln Arg Leu Asn Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 25
<211> LENGTH: 152
<212> TYPE: PRT
<213> ORGANISM: Artificial sequence
<220> FEATURE:
<223> OTHER INFORMATION: Artificially synthesized Affilin-142441

<400> SEQUENCE: 25

Met Gln Ile Phe Val Lys Thr Leu Thr Asn Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                    85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 26
<211> LENGTH: 152
<212> TYPE: PRT
<213> ORGANISM: Artificial sequence
<220> FEATURE:
<223> OTHER INFORMATION: Artificially synthesized Affilin-142439

<400> SEQUENCE: 26

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Ala Gly Lys
        35                  40                  45

Gln Leu Glu Tyr Gly Arg Thr Leu Ser Asp Tyr Asn Ile Gln Lys Glu
    50                  55                  60
```

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 27
<211> LENGTH: 152
<212> TYPE: PRT
<213> ORGANISM: Artificial sequence
<220> FEATURE:
<223> OTHER INFORMATION: Artificially synthesized Affilin-141931

<400> SEQUENCE: 27

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Gln Ile Phe
65                  70                  75                  80

Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 28
<211> LENGTH: 152
<212> TYPE: PRT
<213> ORGANISM: Artificial sequence
<220> FEATURE:
<223> OTHER INFORMATION: Artificially synthesized Affilin-141926

<400> SEQUENCE: 28

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Ala Gly Lys
        35                  40                  45

Gln Leu Glu Asp Gly Arg Thr Leu Ser Asp Tyr Asn Ile Gln Lys Glu
    50                  55                  60

```
Ser Thr Leu Trp Leu Tyr Leu Thr Trp Tyr Ala Ala Met Arg Ile Phe
 65                  70                  75                  80

Val Thr Thr His Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 29
<211> LENGTH: 152
<212> TYPE: PRT
<213> ORGANISM: Artificial sequence
<220> FEATURE:
<223> OTHER INFORMATION: Artificially synthesized Affilin-141869

<400> SEQUENCE: 29

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Gln Ile Phe
 65                  70                  75                  80

Val Thr Thr His Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 30
<211> LENGTH: 152
<212> TYPE: PRT
<213> ORGANISM: Artificial sequence
<220> FEATURE:
<223> OTHER INFORMATION: Artificially synthesized Affilin-141890

<400> SEQUENCE: 30

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Thr Leu Ala Phe Ala Gly Lys
        35                  40                  45

Gln Leu Glu Asp Gly Arg Thr Leu Ser Asp Tyr Asn Ile Gln Lys Glu
```

Ser Thr Leu Trp Leu Tyr Leu Thr Trp Tyr Ala Ala Met Gln Ile Phe
65                  70                  75                  80

Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 31
<211> LENGTH: 152
<212> TYPE: PRT
<213> ORGANISM: Artificial sequence
<220> FEATURE:
<223> OTHER INFORMATION: Artificially synthesized Affilin-141912

<400> SEQUENCE: 31

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Val Pro Pro Asp Gln Gln Thr Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu Phe Leu Tyr Leu Tyr Val Ser Ala Ala Met Gln Ile Phe
65                  70                  75                  80

Val Leu Thr Asp Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Glu Leu Trp Arg Asn Leu His
    130                 135                 140

Leu Val Leu Arg Leu Arg Ala Ala
145                 150

<210> SEQ ID NO 32
<211> LENGTH: 152
<212> TYPE: PRT
<213> ORGANISM: Artificial sequence
<220> FEATURE:
<223> OTHER INFORMATION: Artificially synthesized Affilin-141935

<400> SEQUENCE: 32

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Asp Gly Ile Pro Pro Asp Gln Gln Thr Leu Thr Phe Ala Gly Lys
            35                  40                  45

-continued

```
Gln Leu Glu Asp Gly Arg Thr Leu Ser Asp Tyr Asn Ile Gln Lys Glu
 50                  55                  60

Ser Thr Leu Tyr Leu Tyr Leu Gly Ile Ser Ala Ala Met Gln Ile Phe
 65                  70                  75                  80

Val Ile Thr Ser Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
                115                 120                 125

Gly Arg Thr Leu Ser Asp Tyr Asn Ile Glu Leu Trp Arg Asn Leu His
                130                 135                 140

Leu Val Leu Arg Leu Arg Ala Ala
145                 150

<210> SEQ ID NO 33
<211> LENGTH: 152
<212> TYPE: PRT
<213> ORGANISM: Artificial sequence
<220> FEATURE:
<223> OTHER INFORMATION: Artificially synthesized Affilin-142465

<400> SEQUENCE: 33

Met Gln Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Leu Leu Ser Phe Ala Gly Lys
                 35                  40                  45

Gln Leu Glu Asp Gly Arg Thr Leu Ser Asp Tyr Asn Ile Gln Lys Glu
 50                  55                  60

Ser Thr Leu His Leu Trp Leu Gly Val Arg Ala Ala Met Gln Ile Phe
 65                  70                  75                  80

Val Asn Thr Glu Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
                115                 120                 125

Gly Arg Thr Leu Ser Asp Tyr Asn Ile Ser Glu Trp Ala Ile Leu His
                130                 135                 140

Leu Val Leu Arg Leu Arg Ala Ala
145                 150

<210> SEQ ID NO 34
<211> LENGTH: 152
<212> TYPE: PRT
<213> ORGANISM: Artificial sequence
<220> FEATURE:
<223> OTHER INFORMATION: Artificially synthesized Affilin-142655

<400> SEQUENCE: 34

Met Gln Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Leu Asp
                 20                  25                  30

Lys Glu Gly Ile Pro Pro Asp Gln Gln Ser Leu Val Phe Ala Gly Lys
                 35                  40                  45
```

Gln Leu Glu Asp Gly Arg Thr Leu Ser Val Tyr Asn Ile Gln Lys Glu
            50                  55                  60

Ser Thr Leu Tyr Leu Tyr Leu Phe Ser Arg Ala Ala Met Arg Ile Phe
 65                  70                  75                  80

Val Leu Thr Asp Thr Gly Lys Thr Ile Thr Leu Glu Val Glu Ser Ser
                 85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
                115                 120                 125

Gly Arg Thr Leu Ser Asp Tyr Asn Ile Arg Gly Trp Ser Leu Leu His
                130                 135                 140

Leu Val Leu Arg Leu Arg Ala Ala
145                 150

<210> SEQ ID NO 35
<211> LENGTH: 152
<212> TYPE: PRT
<213> ORGANISM: Artificial sequence
<220> FEATURE:
<223> OTHER INFORMATION: Artificially synthesized Affilin-142418

<400> SEQUENCE: 35

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Ser Leu Val Phe Ala Gly Lys
                 35                  40                  45

Gln Leu Glu Asp Gly Arg Thr Leu Ser Asp Tyr Asn Ile Gln Ile Glu
            50                  55                  60

Ser Thr Leu Tyr Leu Tyr Leu Phe Ser Arg Ala Ala Met Arg Ile Phe
 65                  70                  75                  80

Val Leu Thr Asp Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
                115                 120                 125

Gly Arg Thr Leu Ser Asp Tyr Asn Ile Arg Gly Trp Ser Leu Leu His
                130                 135                 140

Leu Val Leu Arg Leu Arg Ala Ala
145                 150

<210> SEQ ID NO 36
<211> LENGTH: 152
<212> TYPE: PRT
<213> ORGANISM: Artificial sequence
<220> FEATURE:
<223> OTHER INFORMATION: Artificially synthesized Affilin-142627

<400> SEQUENCE: 36

Met Gln Ile Phe Val Lys Thr Leu Thr Gly Lys Thr Ile Thr Val Glu
 1               5                  10                  15

Val Glu Pro Cys Asp Thr Ile Glu Asn Val Lys Ala Lys Ile Gln Asp
                 20                  25                  30

Lys Glu Gly Ile Pro Pro Asp Gln Gln Ser Leu Val Phe Ala Gly Lys

```
                35                  40                  45
Gln Leu Glu Asp Gly Arg Thr Leu Ser Asp Tyr Asn Ile Gln Lys Glu
 50                  55                  60

Ser Thr Leu Tyr Leu Tyr Leu Phe Ser Arg Ala Ala Met Arg Ile Phe
 65                  70                  75                  80

Val Leu Thr Asp Thr Gly Lys Thr Ile Thr Leu Glu Val Glu Pro Ser
                 85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Ser Glu Trp Ala Ile Leu His
        130                 135                 140

Leu Val Leu Arg Leu Arg Ala Ala
145                 150

<210> SEQ ID NO 37
<211> LENGTH: 152
<212> TYPE: PRT
<213> ORGANISM: Artificial sequence
<220> FEATURE:
<223> OTHER INFORMATION: Artificially synthesized Affilin-141975

<400> SEQUENCE: 37

Met Gln Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Ser Leu Val Phe Ala Gly Lys
         35                  40                  45

Gln Leu Glu Tyr Gly Arg Thr Leu Ser Asp Tyr Asn Ile Gln Lys Glu
 50                  55                  60

Ser Thr Leu Tyr Leu Tyr Leu Phe Ser Arg Val Ala Met Arg Ile Phe
 65                  70                  75                  80

Val Leu Thr Asp Thr Gly Lys Thr Ile Thr Leu Glu Val Glu Pro Asn
                 85                  90                  95

Asp Thr Ile Glu Asn Val Lys Ala Lys Ile Gln Asp Lys Glu Gly Ile
            100                 105                 110

Pro Ser Asp Gln Gln Arg Leu Ile Trp Ala Gly Lys Gln Leu Glu Asp
            115                 120                 125

Gly Arg Ala Leu Ser Asp Tyr Asn Ile Ser Glu Trp Ala Ile Leu His
        130                 135                 140

Leu Val Leu Arg Leu Arg Ala Ala
145                 150

<210> SEQ ID NO 38
<211> LENGTH: 152
<212> TYPE: PRT
<213> ORGANISM: Artificial sequence
<220> FEATURE:
<223> OTHER INFORMATION: Artificially synthesized Affilin-141884

<400> SEQUENCE: 38

Met Gln Ile Phe Val Lys Thr Leu Thr Gly Lys Thr Ile Thr Leu Glu
  1               5                  10                  15

Val Glu Pro Ser Asp Thr Ile Glu Asn Val Arg Ala Lys Ile Gln Asp
             20                  25                  30
```

Lys Glu Gly Ile Pro Pro Asp Gln Gln Thr Leu Ala Phe Ala Gly Lys
            35                  40                  45

Gln Leu Glu Asp Gly Arg Thr Leu Ser Asp Tyr Asn Ile Gln Lys Glu
 50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Ser Glu Trp Ala Ile Leu His
            130                 135                 140

Leu Val Leu Arg Leu Arg Ala Ala
145                 150

<210> SEQ ID NO 39
<211> LENGTH: 152
<212> TYPE: PRT
<213> ORGANISM: Artificial sequence
<220> FEATURE:
<223> OTHER INFORMATION: Artificially synthesized Affilin-144160
      CD3-binding protein

<400> SEQUENCE: 39

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Trp Leu Trp Phe Ala Gly Lys
            35                  40                  45

Gln Leu Glu Asp Gly Arg Thr Leu Ser Asp Tyr Asn Ile Gln Lys Glu
 50                  55                  60

Ser Thr Leu Lys Leu Trp Leu Val Asp Lys Ala Ala Met Gln Ile Phe
65                  70                  75                  80

Val Tyr Thr Arg Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Ala Leu Glu Ser Gly Leu His
            130                 135                 140

Leu Val Leu Arg Leu Arg Ala Ala
145                 150

<210> SEQ ID NO 40
<211> LENGTH: 152
<212> TYPE: PRT
<213> ORGANISM: Artificial sequence
<220> FEATURE:
<223> OTHER INFORMATION: Artificially synthesized Affilin 143488
      EpCAM-binding protein

<400> SEQUENCE: 40

Met Gln Ile Phe Val Lys Thr Leu Thr Gly Lys Thr Ile Thr Leu Glu
1               5                   10                  15

```
Val Glu Pro Ser Asp Thr Ile Glu Asn Val Lys Ala Lys Ile Gln Asp
            20                  25                  30

Lys Glu Gly Ile Pro Pro Asp Gln Gln Tyr Leu Tyr Phe Ala Gly Lys
            35                  40                  45

Gln Leu Glu Asp Gly Arg Thr Leu Ser Asp Tyr Asn Ile Gln Lys Glu
            50                  55                  60

Ser Thr Leu Lys Leu Tyr Leu Trp Arg Val Ala Ala Met Gln Ile Phe
65                  70                  75                  80

Val Ala Thr Gly Thr Gly Lys Thr Ile Thr Leu Glu Val Glu Pro Ser
                    85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Gly Ser Tyr Gly Tyr Leu His
            130                 135                 140

Leu Val Leu Arg Leu Arg Ala Ala
145                 150

<210> SEQ ID NO 41
<211> LENGTH: 152
<212> TYPE: PRT
<213> ORGANISM: Artificial sequence
<220> FEATURE:
<223> OTHER INFORMATION: Artificially synthesized Affilin-143283
      EpCAM-binding protein

<400> SEQUENCE: 41

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Gln Phe Ala Gly Lys
            35                  40                  45

Gln Leu Glu Asp Gly Arg Thr Leu Ser Asp Tyr Asn Ile Gln Lys Glu
            50                  55                  60

Ser Thr Leu Gly Leu Leu Leu Thr Gln Arg Ala Ala Met Gln Ile Phe
65                  70                  75                  80

Val Tyr Thr Asn Thr Gly Lys Thr Ile Thr Leu Glu Val Glu Pro Ser
                    85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Phe Arg Phe Gln His Leu His
            130                 135                 140

Leu Val Leu Arg Leu Arg Ala Ala
145                 150

<210> SEQ ID NO 42
<211> LENGTH: 152
<212> TYPE: PRT
<213> ORGANISM: Artificial sequence
<220> FEATURE:
<223> OTHER INFORMATION: Artificially synthesized Affilin-142265
      EGFR-binding protein

<400> SEQUENCE: 42
```

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Glu Leu Thr Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Glu Leu Tyr Ala Lys Ala Met Gln Ile Phe
65                  70                  75                  80

Val Gln Thr Ile Thr Gly Lys Thr Ile Thr Leu Glu Val Glu Pro Ser
            85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Thr Arg Leu Val Trp Leu His
        130                 135                 140

Leu Val Leu Arg Leu Arg Ala Ala
145                 150

<210> SEQ ID NO 43
<211> LENGTH: 152
<212> TYPE: PRT
<213> ORGANISM: Artificial sequence
<220> FEATURE:
<223> OTHER INFORMATION: Artificially synthesized di-Ubiquitin

<400> SEQUENCE: 43

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
            85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
            115                 120                 125

Gly Arg Thr Leu Ser Asp Tyr Asn Ile Gln Lys Glu Ser Thr Leu His
        130                 135                 140

Leu Val Leu Arg Leu Arg Gly Gly
145                 150

<210> SEQ ID NO 44
<211> LENGTH: 4
<212> TYPE: PRT
<213> ORGANISM: Artificial sequence
<220> FEATURE:
<223> OTHER INFORMATION: Artificially synthesized peptide linker

<400> SEQUENCE: 44

```
Ser Gly Gly Gly
1

<210> SEQ ID NO 45
<211> LENGTH: 4
<212> TYPE: PRT
<213> ORGANISM: Artificial sequence
<220> FEATURE:
<223> OTHER INFORMATION: Artificially synthesized peptide linker

<400> SEQUENCE: 45

Gly Gly Gly Ser
1
```